United States Patent
Bökel et al.

(10) Patent No.: US 8,771,682 B2
(45) Date of Patent: Jul. 8, 2014

(54) METHODS AND COMPOSITIONS FOR REDUCING INTERLEUKIN-4 OR INTERLEUKIN-13 SIGNALING

(75) Inventors: Christian Bökel, Dresden (DE); Thomas Weidemann, Desden (DE)

(73) Assignee: Technische Universtität Dresden, Dresden (DE)

( * ) Notice: Subject to any disclaimer, the term of this patent is extended or adjusted under 35 U.S.C. 154(b) by 111 days.

(21) Appl. No.: 13/457,029

(22) Filed: Apr. 26, 2012

(65) Prior Publication Data

US 2013/0084275 A1 Apr. 4, 2013

Related U.S. Application Data

(60) Provisional application No. 61/478,939, filed on Apr. 26, 2011.

(51) Int. Cl.
*A61K 38/00* (2006.01)

(52) U.S. Cl.
USPC ............ 424/94.5; 514/293; 514/211.08; 514/406; 514/185; 514/235.2; 514/1.1; 514/44; 514/275; 514/258.1; 435/29; 435/194; 435/375; 544/128; 544/278; 544/324; 536/24.5; 530/300; 546/82; 546/10; 540/545; 548/377.1

(58) Field of Classification Search
CPC ............ Y10S 514/826; Y10S 514/886; Y10S 514/887; C12N 2501/2304; C12N 2501/2313
USPC ............ 424/94.5; 514/235.2, 1.1, 44, 275, 514/258.1, 293, 211.08, 406, 185; 435/29, 435/194, 375; 544/128, 278, 324; 536/24.5; 530/300; 546/82, 10; 540/545; 548/377.1

See application file for complete search history.

(56) References Cited

U.S. PATENT DOCUMENTS

| | | | |
|---|---|---|---|
| 7,514,432 B2 | 4/2009 | Leblond et al. | |
| 7,612,080 B2 | 11/2009 | Zheng et al. | |
| 7,635,754 B2 | 12/2009 | Boisvert et al. | |
| 2002/0045564 A1 | 4/2002 | Van Eyk et al. | |
| 2003/0165992 A1 | 9/2003 | Adra et al. | |
| 2007/0212308 A1 | 9/2007 | Tepper et al. | |

FOREIGN PATENT DOCUMENTS

| | | |
|---|---|---|
| EP | 1597253 B1 | 8/2006 |
| WO | 0212242 A2 | 2/2002 |
| WO | 2007031878 A2 | 3/2007 |
| WO | 2007072153 A2 | 6/2007 |

OTHER PUBLICATIONS

Vikis et al (Genes Dev. 2002 16: 836-845).*
"Nanopeptide Corresponding to the sequence 27-35 of the Mature Human IL-2 Efficiently Competes with rIL-2 for Binding to Thymocyte Receptors," Immunology Letters, 31:285-288 (1992).
"SCH 51344 Inhibits ras Transformation by a Novel Mechanism," Cancer Res, 55:5106-5117 (1995).
"Pulmonary Expression of Interleukin-13 Causes Inflammation, Mucous Hypersecretion, Subepithelial Fibrosis, Physiologic Abnormalities, and Eotaxin Production," J Clin Invest 103:779-788 (1999).
"Solubble IL-4 Receptor Inhibits Airway Inflammation Following Allergen Challenge in a Mouse Model of Asthma," J Immunol 164:1086-1095 (2000).
"The K252a Derivatives, Inhibitors for the PAK/MLK Kinase Family, Selectively Block the Growth of RAS Transformants," Cancer J 8:328-335 (2002).
"Rational Design and Characterization of a Rac GTPase=specific Small Molecule Inhibitor," PNAS 101:7618-7623 (2004).
"Specificity and Mechanism of Action of EHT 1864, a Novel Small Molecule Inhibitor of Rac Family Small GTPases," J Biol Chem 282:35666-25678 (2007).
"Clathrin-independent Endocytosis Used by the IL-2 Receptor is Regulated by Rac1, Pak1 and Pak2," EMBO Reports 9:356-362 (2008).
"An Isoform-selective, Small-molecule Inhibitor Targets the Autoregulatory Mechanism of p21-Activated Kinase," Chem & Biol 15:322-331 (2008).
"Small-molecule p21-activated Kinase Inhibitor PF-3758309 is a Potent Inhibitor of Oncogenic Signaling and Tumor Growth," PNAS 107:9446-9451 (2010).
"Development of Small-molecule Inhibitors of the Group I p21-activated Kinases, Emerging Therapeutic Targets in Cancer," Biochem Pharmacol 80:683-689 (2010).

* cited by examiner

*Primary Examiner* — Jason Sims
*Assistant Examiner* — Ibrahim D Bori
(74) *Attorney, Agent, or Firm* — Mastermind IP Law P.C.; Diane L. Gardner

(57) ABSTRACT

The present invention relates generally to methods and compositions for reducing Interleukin-4 or Interleukin-13 signaling, in particular to treat asthma and atopic dermatitis. The inventors have found that Rac/PAK mediated endocytosis of the ligand bound type I (IL-4R with the chains IL-4Ra and IL-2-Rg) and/or type II receptor (IL-13R with the chains IL-4Ra and IL-13Ra1) is needed for the IL-4 and/or IL-13 mediated activation of downstream signalling events including phosphorylation of Stat family transcrition factors. These discoveries enable new methods of screening compounds that modulate Interleukin-4 and Interleukin-13 signalling, as well as new methods for treating conditions characterized by increased Interleukin-4 and Interleukin-13 levels. These conditions include inflammatory conditions, asthma bronchiale, atopic dermatitis, allergies, atopic syndromes, allergic rhinitis, and th2-induced conditions.

13 Claims, 9 Drawing Sheets

State of the Art

METHODS AND COMPOSITIONS FOR REDUCING INTERLEUKIN-4 OR INTERLEUKIN-13 SIGNALING

CROSS-REFERENCE TO RELATED APPLICATION

This application claims priority from U.S. Provisional Patent Application No. 61/478,939 filed on Apr. 26, 2011, incorporated herein by reference.

REFERENCE TO A SEQUENCE LISTING SUBMITTED AS A TEXT FILE VIA EFS-WEB

The official copy of the sequence listing is submitted concurrently with the specification as a text file via EFS-Web, in compliance with the American Standard Code for Information Interchange (ASCII), with a file name of 0089-P001001SEQ_LISTING.txt, a creation date of Apr. 18, 2011, and a size of 9.72 KB. The sequence listing filed via EFS-Web is part of the specification and is hereby incorporated by reference herein in its entirety.

BACKGROUND

Interleukin-4 (IL-4) and Interleukin-13 (IL-13) are cytokines involved in several inflammatory diseases caused by immune dysregulation, most notably asthma and atopic dermatitis. Studies conducted with animals deficient in either cytokine, or employing reagents that neutralize either IL-4 or IL-13 function, have elucidated the important role these cytokines play in regulating the primary and secondary immune response leading to airway inflammation and airway hyper-responsiveness (Zhu et al. 1999. J. Clin. Invest. 103: 779-788, Henderson et al. 2000 J. Immunol. 164: 1086-1095). Cumulatively, these data suggest that IL-4 and IL-13 have overlapping as well as independent roles in the allergic airways response.

IL-4 is increasingly appreciated as the pivotal cytokine initiating the "Th2-type" inflammatory response forming the underling milieu necessary for the development of atopy and asthma. IL-4 effects include activation, proliferation and differentiation of T and B cells. During proliferation of B-lymphocytes, IL-4 acts as a differentiation factor by regulating class switching from IgG to the IgE, thus encouraging the development of allergic reactions.

IL-13 is now appreciated as the more probable downstream effector cytokine. IL-13 dominate effects include induction of airways hyperresponsiveness (AHR) and goblet cell hyperplasia, both cardinal features of asthma. However, there is considerable redundancy in the effects of these two cytokines. The redundancy in effects associated with the binding and signaling of these two cytokines can be explained by their sharing of common receptors.

The IL-4 receptor alpha chain (IL-4Ra) is known to form two distinct ternary complexes with ligands and coreceptors. The type I receptor complex (IL-4R) is typically formed in lymphoid cells and consists of the IL-4Ra chain and the IL-2 receptor common gamma chain (IL-2Rg). It binds specifically to and transduces signals by the IL-4 cytokine ligand. In nonlymphoid cells, e.g. airway epithelial cells, IL-4R alpha chain forms a complex with the IL-13 receptor alpha chain 1(IL-13Ra1). This so called type II receptor (also called IL-13R) binds to and is activated by both IL-4 and IL-13.

The receptor chains (IL-4Ra, IL-13Ra1 and IL-2Rg) interact specifically with downstream nonreceptor tyrosine kinases of the Janus kinase (Jak) family, with the IL-4Ra associating with Jak1, the IL-2Rg chain with Jak3, and the IL-13Ra chain with Tyk2. Upon ligand binding to the receptor, these kinases are activated by an as yet not understood mechanism, and cause phosphorylation of the receptor chains, the kinases themselves, and eventually of the transcription factors of the Stat family that are recruited to the phosphorylated receptors.

While asthma is generally defined as an inflammatory disorder of the airways, clinical symptoms arise from intermittent air flow obstruction. It is a chronic disabling disorder that appears to be increasing in prevalence and severity. It is estimated that 30-40% of the population suffers with atopy, and 15% of children and 5% to 10% of adults in the population suffer from asthma.

Atopy or atopic syndrome is a predisposition toward developing certain allergic hypersensitivity reactions. A patient with atopy typically presents with one or more of the following: eczema (atopic dermatitis or neurodermatitis), allergic rhinitis (hayfever), allergic conjunctivitis, or allergic asthma. Patients with atopy also have a tendency to have food allergies.

Current treatments for these diseases involve interference with downstream effector molecules such as anti-IgE as well as immune suppressing agents (i.e. corticosteroids). However, these approaches are not efficient in all patients and are associated with, often severe, side effects.

Beta agonists reduce the symptoms of asthma, i.e. transiently improve pulmonary functions, but do not affect the underlying inflammation so that lung tissue remains in jeopardy. In addition, constant use of beta agonists results in desensitization, which reduces their efficacy and safety. The agents that can diminish the underlying inflammation, the anti-inflammatory steroids, have their own known list of disadvantages that range from immunosuppression to bone loss.

Because of the problems associated with conventional therapies, alternative treatment strategies have been evaluated. Glycophorin A, cyclosporin, and a non-peptide fragment of IL-2, all inhibit interleukin-2 dependent T lymphocyte proliferation and, therefore, IL-9 production; however, they are known to have many other effects. While these agents may represent alternatives to steroids in the treatment of asthmatics (Zav'yalov et al. 1992. Immunol. Lett. 31:285-288 56), they inhibit interleukin-2 dependent T lymphocyte proliferation and potentially critical immune functions associated with homeostasis.

It is known that a dynamin dependent, clathrin independent pathway is responsible for the clearance of IL-2beta receptor following ligand binding, and that this pathway is dependent upon the activity of the small G proteins RhoA and Rac1, and the kinases PAK1 and PAK2 (Grassart A et al. 2008 EMBO Rep. 9(4):356-62). Rac and PAK family kinases are further known to play a role in macropinocytosis and type I phagocytosis, i.e. internalization of immunoglobulin activated Fe-receptors (Qualmann B, Mellor H 2003, Biochem J 371, 233-241), EphrinB receptors (Marston D j et al. 2003. Nature Cell Biology 5, 879-888), and cadherins (Yap A S et al. 2007. Current Opinion in Cell Biology 19:508-514). It is known that PAK promotes morphological changes by acting downstream of Rac (Oelschlager, T. A. et al 1993 EMBO J. 17:4328-4339).

US2002/045564A1 relates to a method of modulating smooth Muscle contraction, comprising administering a PAK3 modulating agent to a subject such that modulation of smooth muscle contraction occurs.

US 2003/0165992A relates to a method for detecting a predisposition to asthma or atopy in an individual, the method comprising: analyzing a biological specimen from said individual for the presence of a Il-13 Gln110Arg variant; wherein the presence of said variant is indicative of an increased susceptibility to asthma or atopy.

US2007/0212308A relates to a method of treating asthma comprising administering to a subject in need thereof, a pharmaceutical composition containing a therapeutically effective amount of a mutant human IL-4 protein.

U.S. Pat. No. 7,635,754 discloses a chimeric polypeptide, comprising an interleukin-4 (IL-4) mutein receptor antagonist operatively linked to an interleukin-9 (IL-9) mutein receptor antagonist and wherein the chimeric polypeptide reduces or inhibits the association of an interleukin with an IL-4 receptor, an IL-9 receptor, an interleukin-13 (IL-13) receptor, or a combination thereof, in particular for the treatment of asthma.

What is needed in the art is the identification of a pathway critical to the development of asthma and atopy that allows the development of novel therapeutic approaches. The objective of the invention is further to provide agents for the treatment of asthma and atopy.

SUMMARY OF THE INVENTION

The present invention is based on the experimental observation that IL-4 and IL-13 signaling requires Rac/PAK mediated endocytosis in the target cells.

The inventors have found that Rac/PAK mediated endocytosis of the ligand bound type I (IL-4R with the chains IL-4Ra and IL-2-Rg) and/or type II (IL-13R with the chains IL-4Ra and IL-13Ra1) receptor is needed for the IL-4 and/or IL-13 mediated activation of downstream signalling events including phosphorylation of Stat family transcrition factors. This is surprising as normally endocytosis is a mechanism of down regulating the signal by reducing the receptor concentration on the surface of the cell.

DESCRIPTION OF THE DRAWINGS

FIG. 15 shows the bottom membrane of a cell at time point 0 min after temperature release (onset of endocytosis). FIG. 16 shows the Bottom membrane of the same cell at time point 7 min after temperature release. FIG. 17 shows the central cross-section of another cell at time point 7 min after temperature release. FIG. 18 shows the bottom membrane of cells pre-incubated with 50 μmol/l EHT-1864 at time point 21 min after the temperature release. The figure illustrates that transport of the Alexa647-labeled ligand is reduced. FIG. 19 shows the central cross-section of another group of cells, pre-incubated with 50 μmol/l EHT-1864 at time point 22 min after the temperature release. This figure is again illustrating the reduced uptake of the labeled ligand.

DETAILED DESCRIPTION

The present invention is based on the experimental observation that IL-4 and IL-13 signaling requires Rac/PAK mediated endocytosis in the target cells.

The inventors have found that Rac/PAK mediated endocytosis of the ligand bound type I (IL-4R with the chains IL-4Ra and IL-2-Rg) and/or type II (IL-13R with the chains IL-4Ra and IL-13Ra1) receptor is needed for the IL-4 and/or IL-13 mediated activation of downstream signalling events including phosphorylation of Stat family transcrition factors. This is surprising as normally endocytosis is a mechanism of down regulating the signal by reducing the receptor concentration on the surface of the cell.

In particular the inventors have found that IL-2-2g/Jak3 complexes reside in endosomes and that endocytosis defective mutants in Jak3 are signaling dead. Further, activated IL-4 receptors accumulate in the Jak3 decorated endosomes following ligand exposure. This is consistent with the observation that Rac/PAK mediated endocytosis is a prerequisite for IL-4/IL-13 signaling.

Figure 9:
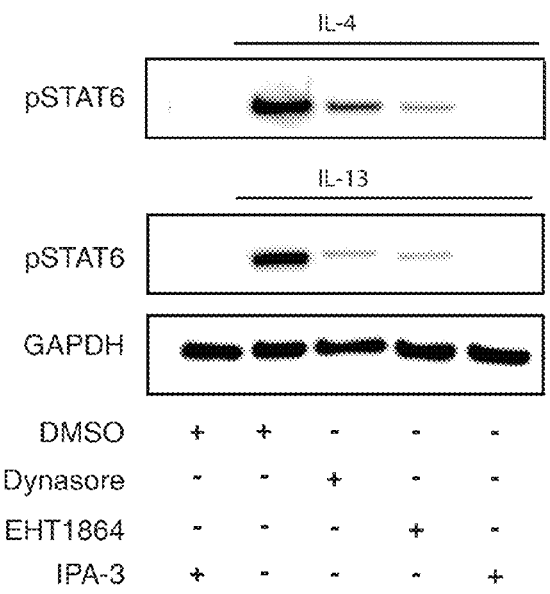
FIG. 9 shows the results of effect of inhibitors Dynasore, as well as EHT-1864 and IP-3 (inhibiting Rac/Pak driven endocytosis) on IL-4 and IL-13 signaling in epithelial cells HEK293T cells transfected with Stat6.
Figure 13:
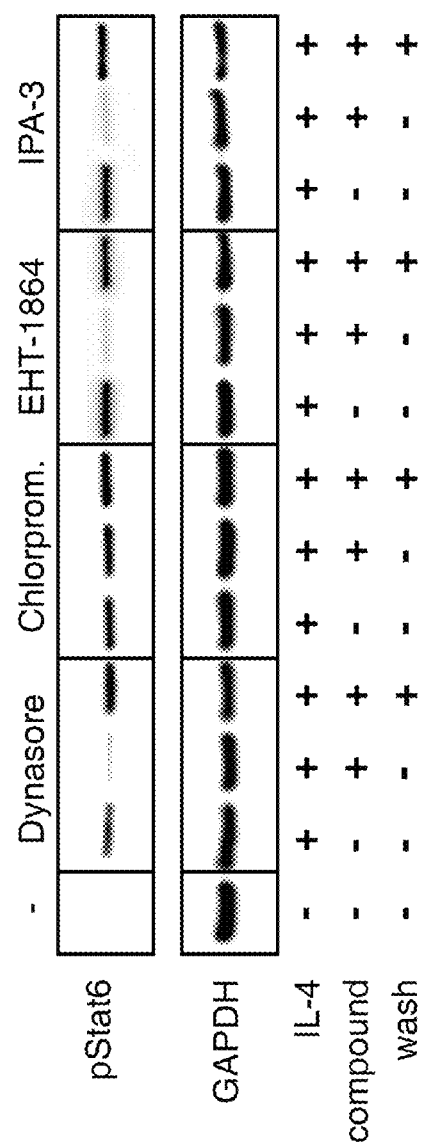
FIG. 13 shows the effect of the inhibitors of Rac/Pak driven endocytosis, Dynasore, as well as EHT-1864 and IPA-3, on IL-4 signaling in HEK293T cells reconstituted with IL-2Rg and Jak3 (type I signaling). Again, chlorpromazine was used as a control.

The inventors have further demonstrated that blocking Rac1 mediated endocytosis strongly but reversibly reduces Stat6 phosphorylation downstream of both type I (IL-4R) and type II (IL-13R) receptor activation by IL-4 and/or -13. As shown in FIGS. 9 and 13 this blocking of IL-4/IL-13 signaling could either be achieved by inhibiting Rac activation using an inhibitor of Rac (e.g. EHT-1864), by blocking the downstream effector kinase Pak1/2 (e.g. with IPA-1), or by preventing dynamin-dependent scission of endocytic vesicles from the plasma membrane (e.g. using Dynasore).

Importantly, inhibition of clathrin-mediated endocytosis, which shares a subsequent requirement for dynamin function with Rac-mediated endocytosis, had no effect on phospho-Stat6 levels.

Pharmacological inhibition of Rac/Pak driven endocytosis is therefore a novel approach for blocking IL-4 and -13 signaling and a novel therapeutic approach for treatment of conditions showing an excessive IL-4 and -13 signaling, in particular inflammatory diseases associated with a deregulation of the immune system, such as asthma or atopic dermatitis.

In one aspect the present invention provides a method for reducing Interleukin-4 or Interleukin-13 signaling in a cell or subject (in particular a mammal or patient) comprising administering an inhibitor of Rac/Pak driven endocytosis in an amount sufficient to reduce or inhibit endocytosis of IL-4R or IL-13R and preferably in an amount sufficient to reduce or inhibit subsequent phosphorylation of Stat family transcription factors.

In another aspect the invention relates to a method of treating a condition characterized by increased Interleukin-4 or Interleukin-13 levels in a subject in need thereof comprising administering an inhibitor of Rac/Pak driven endocytosis in a therapeutically effective amount.

The condition characterized by increased Interleukin-4 or Interleukin-13 levels is preferably selected from inflammatory conditions, asthma bronchiale, atopic dermatitis, and allergies, atopic syndromes, allergic rhinitis and other th2-induced conditions.

In another aspect the present invention provides a method of treating atopic dermatitis in a subject in need thereof comprising administering an inhibitor of Rac/Pak driven endocytosis in a therapeutically effective amount.

In yet another aspect the present invention provides agents inhibiting Rac/Pak driven endocytosis for use in the treatment of dermatitis, in particular atopic dermatitis. The therapeutically effective amount is preferably an amount sufficient to reduce or inhibit endocytosis of IL-4R or IL-1312 and preferably in an amount sufficient to reduce or inhibit subsequent phosphorylation of Stat family transcription factors in particular in endothelial cells of the affected organ, e.g. airway epithel or the skin.

The term "subject" as used herein refers to any individual or patient to which the subject methods are performed. Generally the subject is human, although as will be appreciated by those in the art, the subject may be an animal. Thus, other animals, including mammals such as rodents (including mice, rats, hamsters and guinea pigs), cats, dogs, rabbits, farm animals including cows, horses, goats, sheep, pigs, etc., and non human primates (including monkeys, chimpanzees, orangutans and gorillas) are included within the definition of subject.

A "subject in need thereof" is a person or animal suffering from asthma, atopy, atopic dermatitis, and allergies, atopic syndromes, allergic rhinitis or other conditions characterized by increased Interleukin-4 or Interleukin-13 levels, in particular th2-induced conditions.

The term "asthma" (or asthma bronchiale) is used herein to generally describe a chronic respiratory disease, in particular arising from allergies, that is characterized by sudden recurring attacks of labored breathing, chest constriction, and coughing. In a typical asthmatic reaction, IgE antibodies predominantly attach to mast cells that lie in the lung interstitium in close association with the bronchioles and small bronchi. An antigen entering the airway will thus react with the mast cell-antibody complex, causing release of several substances, including, but not limited to interleukin cytokines, chemokines and arachodonic acid derived mediators, resulting in bronchoconstriction, airway hyperreactivity, excessive mucus secretion and airway inflammation. Thus, in certain embodiments of the invention, the treatment of asthma may include the treatment of airway hyperreactivity and/or the treatment of lung inflammation.

The term "antigen" as used herein refers to any substance that when introduced into the body stimulates the production of an antibody. Antigens include insect, animal and plant proteins, toxins, bacteria, foreign blood cells, and the cells of transplanted organs.

"Allergens" refer to any substances that cause an allergic immune reaction in a subject. Typically, allergens are from foods, plants, insects or animals that inflame the airway and cause mucus production and bronchoconstriction.

The term "atopy" (or atopic syndrome) is used herein to generally describe a disease showing local allergic hypersensitivity reactions. A subject with atopy typically presents with one or more of the following: eczema (atopic dermatitis or neuro dermatitis), allergic rhinitis (hayfever), allergic conjunctivitis, or allergic asthma.

"Atopic dermatitis" (or neuro dermatitis) is an inflammatory, chronically relapsing, non-contagious and pruritic skin disorder. The skin of a patient with atopic dermatitis reacts abnormally and easily to irritants, food, and environmental allergens and becomes red, flaky and very itchy. It also becomes vulnerable to surface infections caused by bacteria. The skin on the flexural surfaces of the joints (for example inner sides of elbows and knees) are the most commonly affected regions. Although atopic dermatitis can theoretically affect any part of the body, it tends to be more frequent on the hands and feet, on the ankles, wrists, face, neck and upper chest. Atopic dermatitis can also affect the skin around the eyes, including the eyelids.

Atopic dermatitis most often begins in childhood before age 5 and may persist into adulthood. For some, it flares periodically and then subsides for a time, even up to several years: Yet, it is estimated that 75% of the cases of atopic dermatitis improve by the time children reach adolescence, whereas 25% continue to have difficulties with the condition through adulthood. In most patients, the usual symptoms that occur with this type of dermatitis are aggravated by a Staphylococcus aureus infection, dry skin, stress, low humidity and sweating, dust or sand or cigarette smoke. Also, the condition can be worsened by having long and hot baths or showers, by solvents, cleaners or detergents, and by wool fabrics or clothing.

Atopic dermatitis is also known as infantile eczema, when it occurs in infants. Infantile eczema may continue into childhood and adolescence and it often involves an oozing, crusting rash mainly on the scalp and face, although it can occur anywhere on the body. The appearance of the rash tends to modify, becoming dryer in childhood and then scaly or thickened in adolescence, while the itching is persistent. Approximately 50% of the patients who develop the condition display symptoms before the age of 1, and 80% display symptoms within the first 5 years of life.

Symptoms may vary from person to person but they are usually present as a red, inflamed, and itchy rash and can quickly develop into raised and painful bumps. The first sign of atopic dermatitis is the red to brownish-gray colored patches that are usually very itchy. Itching may become more intense during the night. The skin may present small and raised bumps which may be crusting or oozing if scratched, which will also worsen the itch. The skin tends to be more sensitive and may thicken, crack or scale. When appearing in the area next to the eyes, scratching can cause redness and swelling around them and sometimes, rubbing or scratching in this area causes patchy loss of eyebrow hair and eyelashes.

The symptoms of atopic dermatitis vary with the age of the patients. Usually, in infants, the condition causes red, scaly, oozy and crusty cheeks and the symptoms may also appear on their legs, neck and arms. Symptoms clear in about half of these children by the time they are 2 or 3 years old. In older children, the symptoms include dry and thick, scaly skin with a very persistent itch, which is more severe than in infants. Adolescents are more likely to develop thick, leathery and dull-looking lesions on their face, neck, hands, feet, fingers or toes.

The terms "administration" or "administering" are defined as including an act of providing a compound or pharmaceutical composition to a subject in need of treatment. The term "therapeutically effective amount" or "effective amount" means the amount of a compound or pharmaceutical composition that will elicit the biological or medical response of a tissue, system, animal or human that is being sought by the researcher, veterinarian, medical doctor or other clinician.

As used herein "Rac/Pak driven endocytosis" is a clathrin-independent, dynamin dependent endocytic pathway. The term in particular refers to Rac/Pak driven endocytosis of the type I (IL-4R) and type II (IL-13R) receptor. Rac is a subfamily of the Rho family of GTPases, small (~21 kDa) signaling G proteins (more specifically GTPases). The family includes Rac1, Rac2, Rac3 and RhoG. As used herein Rac in particular refers to Rac1 and/or Rac2. PAK (p21 activated kinase) refers to a family of kinases, that are targets for the small GTP binding proteins CDC42 and Rac. The family includes PAK1, PAK2, PAK3 and PAK4. As used herein PAK in particular refers to PAK1 and PAK2, as well as PAK4. The PAK Kinases have a relative large ATP binding pocket.

The term "inhibitor of Rac/Pak driven endocytosis" as used herein means an agent (compound or biological) that is effective to inhibit or reduce Rac/Pak driven endocytosis, in particular of the type I (IL-4R) and type II (IL-13R) receptor, by reducing or preventing the activity of Rac or PAK. The "inhibitor of Rac/Pak driven endocytosis" preferably acts on proteins specifically involved in this pathway, in particular Rac or PAK proteins or upstream targets or other targets that are not involved or needed for clathrin dependent endocytosis. This inhibitor may bind to different sites of the proteins and perform a direct antagonist action on the proteins. Preferably the inhibitor prevents the functional interaction between Rac and PAK (such as IPA-3) by directly binding to either the Rac-interaction site on Pak or the PAK interaction site on Rac. Alternatively the PAK inhibitor is a bulky ATP antagonist that does not fit into the ATP binding pocket of most kinases, but fits into the large ATP binding pocket of PAK (such as CEP-1347 and KT D606). The term "inhibitor of Rac/Pak driven endocytosis" also includes agents that reduce expression of the corresponding genes of proteins specifically involved in this pathway, in particular RNAi.

The inhibitor of Rac/Pak driven endocytosis is preferably selected from agents inhibiting Rac-1 or Pak1/2.

The Rac-Inhibitors preferably inhibit Rac1 and are selected from agents disclosed in U.S. Pat. No. 7,514,432, EP1597253B1 and WO2007031878 A2, each document of which the disclosure is hereby incorporated by reference. These Rac-Inhibitors are selected from compounds having a general formula (I):

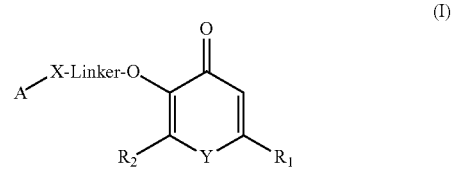

wherein:

$R_1$ is selected from the group consisting of:

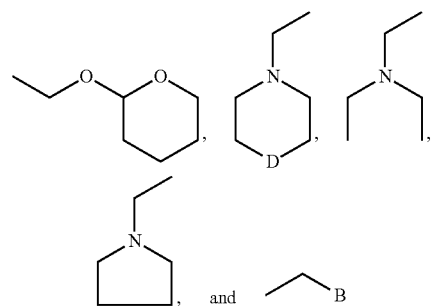

$R_2$ represents a hydrogen atom, an alkyl or alkenyl group containing from 3 to 6 carbon atoms;

B represents an halogen atom, preferably chlorine, a hydroxyl group, a —O—CH$_2$—O—CH$_3$ (MOM) group, a —O—CH$_2$—O—CH$_2$—CH$_2$—O—CH$_3$ (MEM) group, a —OSO$_2$-alkyl group or a —OSi(CH$_3$)$_2$tBu (tBu=tertiary butyl);

D represents an oxygen atom, NR$_3$, CR'R" or a sulfur atom;

X represents an oxygen atom, a sulfur atom or a radical —NR$_4$—;

Y represents an oxygen atom, a sulfur atom or a radical —NR$_4$—;

$R_3$ represents a hydrogen, an alkyl group, a carboxylate group, an acyl group, a carboxamide group or a SO$_2$-alkyl group;

R' and R", identical or different, represent a hydrogen atom or an alkyl radical;

"linker" represents (CH$_2$)$_n$, wherein n represents an integer between 1 and 10 inclusive, optionally interrupted by an heteroatom (preferably N, O, S and P) or a carbonyl group, or an aryldialkyl (preferably xylenyl);

A is optionally substituted and represents a group selected from:

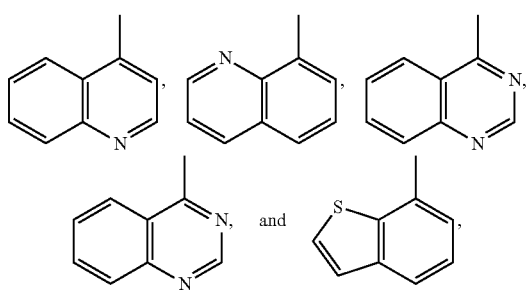

its tautomers, optical and geometrical isomers, racemates, salts, hydrates and mixtures thereof.

A preferred Rac-Inhibitor is:

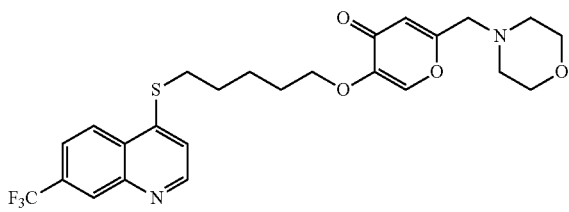 [SMILES: O=c1cc(CN2CCOCC2)occ1OCCCCCSc1ccnc2cc(C(F)(F)F)ccc12]

including its pharmaceutically acceptable salts and prodrugs. This Rac-Inhibitor is named EHT 1864 (5-(5-(7-(Trifluoromethyl)quinolin-4-ylthio)pentyloxy)-2-(morpholinomethyl)-4H-pyran-4-one) and described by Shutes et al. 2007 J Biol Chem. 282(49):35666-78, of which the disclosure is hereby incorporated by reference.

Other preferred Rac-Inhibitors are selected from agents disclosed in U.S. Pat. No. 7,612,080, of which the disclosure is hereby incorporated by reference. These Rac-Inhibitors are selected from compounds having a general formula (II):

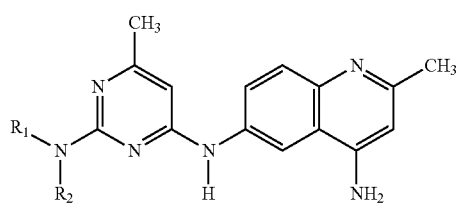

wherein:
$R_1$ to $R_2$ are independently selected from the group consisting of H, —X-Alk, —X-Alk-X', and —X—Y—X'; wherein
X is —$CHR_7R_8$;
X' is —$CHR_7R_8$;
Alk is a $C_2$-$C_{18}$ substituted or unsubstituted hydrocarbon chain;
Y is a $C_2$-$C_8$ substituted or unsubstituted alkylene chain;
$R_6$ is H or ($C_1$-$C_4$) alkyl; and
$R_7$ and $R_8$ are independently selected from the group consisting of H and ($C_1$-$C_4$) alkyl; or a salt of a compound of formula (II).

A preferred Rac-Inhibitor is:

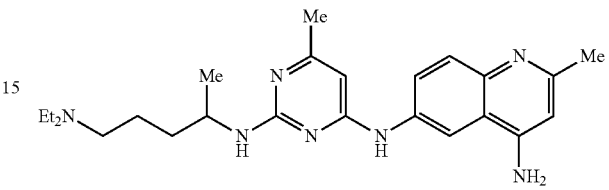

Me = Methyl and Et = Ethyl including its pharmaceutical acceptable salts and prodrugs. This Rac-Inhibitor is named NSC23766 ($N^6$-[2-[[4-(Diethylamino)-1-methylbutyl]amino]-6-methyl-4-pyrimidinyl]-2-methyl-4,6-quinolinediamine) and described by Gao et al. 2004 PNAS 101(20):7618-23, of which the disclosure is hereby incorporated by reference.

Another preferred Rac-Inhibitor is:

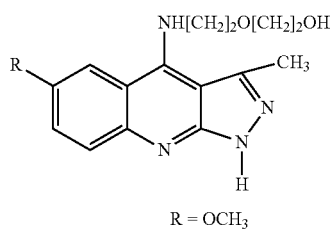

R = $OCH_3$ including its pharmaceutically acceptable salts and prodrugs. This Rac-Inhibitor is named SCH 51344 (CAS Number: 171927-40-5) and described by Kumar et al. 1995 Cancer Research 55. 5106-5117, of which the disclosure is hereby incorporated by reference.

Further Rac-inhibitors are selected from peptides inhibiting Rac1, such as dominant negative Rac, and preferably N17Rac.

Further Rac-Inhibitors are preferably chosen from small hairpin RNA (shRNA) and small interference RNA (shRNA) inhibiting Rac1, most preferably chosen from RNA encoded by one of the following DNA sequences:

| SEQ ID | Sequence | Source (Genbank, NCBI) |
| --- | --- | --- |
| 1 | CACCACTGTCCCAACACTCTT | Pr001115.1 siRNA Probe, sense strand |
| 2 | GAGTGTTGGGACAGTGGTGTT | Pr001115.1 siRNA Probe, antisense strand |
| 3 | GGAGATTGGTGCTGTAAAATT | Pr003104499.1 siRNA probe, sense strand |
| 4 | TTTTACAGCACCAATCTCCTT | Pr003104499.1 siRNA probe, antisense strand |
| 5 | CCTTTGTACGCTTTGCTCATT | Pr003104500.1 siRNA probe, sense strand |

-continued

| SEQ ID | Sequence | Source (Genbank, NCBI) |
|---|---|---|
| 6 | TGAGCAAAGCGTACAAAGGTT | Pr003104500.1 siRNA probe, antisense strand |
| 7 | TGCTGTTGACAGTGAGCGACGACACTGTCACT TGACCAATTAGTGAAGCCACAGATGTAATTGG TCAAGTGACAGTGTCGGTGCCTACTGCCTCGG A | Pr128980.1 shRNA probe V2HS_94788 |
| 8 | TGCTGTTGACAGTGAGCGCGCAATATGCCTCC TTGTATTATAGTGAAGCCACAGATGTATAATA CAAGGAGGCATATTGCTTGCCTACTGCCTCGG A | Pr151934.1 shRNA probe V2HS_202780 |
| 9 | TGCTGTTGACAGTGAGCGCGGACAACTAAAGA TTTCTCAATAGTGAAGCCACAGATGTATTGAG AAATCTTTAGTTGTCCATGCCTACTGCCTCGGA | Pr154431.1 shRNA probe V2HS_57671 |
| 10 | TGCTGTTGACAGTGAGCGCGGGCATTTAATTC ATCTTTAATAGTGAAGCCACAGATGTATTAAA GATGAATTAAATGCCCATGCCTACTGCCTCGG A | Pr159946.1 shRNA probe V2HS_202655 |
| 11 | TGCTGTTGACAGTGAGCGCCCAATGCATTTCCT GGAGAATTAGTGAAGCCACAGATGTAATTCTC CAGGAAATGCATTGGTTGCCTACTGCCTCGGA | Pr160772.1 shRNA probe V2HS_228604 |
| 12 | TGCTGTTGACAGTGAGCGACCATATTGCTCTTC ATATCATTAGTGAAGCCACAGATGTAATGATA TGAAGAGCAATATGGCTGCCTACTGCCTCGGA | Pr161284.1 shRNA probe V2HS_139846 |
| 13 | TGCTGTTGACAGTGAGCGACGTGCCCTACTTG AGAACATTTAGTGAAGCCACAGATGTAAATGT TCTCAAGTAGGGCACGCTGCCTACTGCCTCGG A | Pr161902.1 shRNA probe V2HS_139841 |
| 14 | TGCTGTTGACAGTGAGCGACCATCATCCTAGT GGGAACTATAGTGAAGCCACAGATGTATAGTT CCCACTAGGATGATGGGTGCCTACTGCCTCGG A | Pr163067.1 shRNA probe V2HS_232790 |
| 15 | TGCTGTTGACAGTGAGCGCCCGAGCACTGAAC TTTGCAAATAGTGAAGCCACAGATGTATTTGC AAAGTTCAGTGCTCGGTTGCCTACTGCCTCGG A | Pr170575.1 shRNA probe V2HS_94784 | and complementary sequences thereof, as well as combinations of these RNA. The sequences 1-15 disclosed herein are the DNA-sequences for expressing the siRNA or shRNA.

The PAK-Inhibitors preferably inhibit PAK4 and are selected from agents disclosed in WO2007/072153 A2, of which the disclosure is hereby incorporated by reference. These PAK-Inhibitors are selected from compounds having a general formula (III):

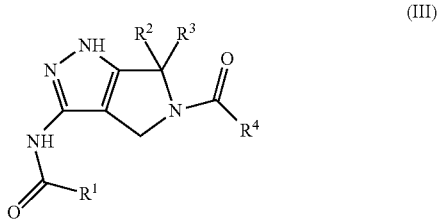

(III)

wherein:

$R^1$ is ethyl, t-butyl, R, -L-($C_3$-$C_{12}$ cycloalkyl), -L-phenyl, -L-(5-12 member heteroaryl), -L-(3-12 member heterocyclyl) and -L-($C_3$-$C_{12}$ unsaturated nonaromatic carbocyclyl);

each $R^2$ and $R^3$ is independently H, $C_1$-$C_8$ alkyl, $C_2$-$C_8$ alkenyl, $C_2$-$C_8$ alkynyl, —($C_1$-$C_3$ alkylene)$_m$-($C_3$-$C_{12}$ cycloalkyl) or —($C_1$$C_6$ perfluoroalkyl), and each $R^2$ and $R^3$ is optionally further substituted or $R^2$ and $R^3$, together with the carbon atom that $R^2$ and $R^3$ attach to, form a ring selected from 3-5 member nonaromatic carbocyclylene and 3-5 member heterocyclylene, and the said ring is optionally further substituted.

Other PAK-Inhibitors preferably inhibiting PAK4 are preferably selected from agents disclosed in WO2002/012242 A2, of which the disclosure is hereby incorporated by reference. These PAK-Inhibitors are selected from compounds having a general formula (IV):

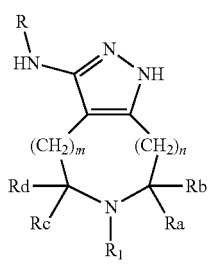

(IV)

wherein R and $R_1$, being the same or different, are independently a hydrogen atom or an optionally substituted group selected from R', —COR', —COOR', —CONHR', —CONR'R", —NH—C (=NH) NHR', —C (=NH) NHR', —SO$_2$R', —SO$_2$NHR' or —SO$_2$NR'R";

wherein R' and R", the same or different, are independently selected from hydrogen or optionally further substituted straight or branched $C_1$-$C_6$ alkyl, aryl, $C_3$-$C_6$ cycloalkyl or aryl $C_1$-$C_6$ alkyl or R' and R" taken together form a $C_4$-$C_6$ alkylene chain;

Ra, Rb, Rc and Rd, being the same or different, are independently selected among hydrogen, optionally further substituted straight or branched C1-C6 alkyl, aryl, aryl C1-C6 alkyl or —CH$_2$O R' groups, wherein R' is as above defined, or Ra and Rb and/or Rc and Rd, taken together with the carbon atom to which they are bonded, form an optionally substituted $C_3$-$C_6$ cycloalkyl group; m and n, each independently, represent 0 or an integer from 1 to 2, provided that m+n is lower than, or equal to, 2 (m+n<2);

and the pharmaceutically acceptable salts thereof.

A preferred PAK-Inhibitor is:

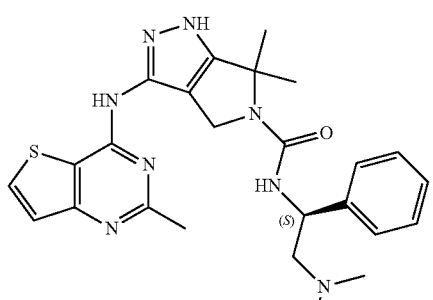

including its pharmaceutically acceptable salts and prodrugs. This PAK-Inhibitor is named PF-3758309 and is described by Murray et al. 2010 PNAS; 107(20):9446-51, of which the disclosure is hereby incorporated by reference.

Other preferred PAK-Inhibitor are described in Yi et al. 2010 Biochem Pharmacol. 80(5):683-9, of which the disclosure is hereby incorporated by reference. These preferred PAK-Inhibitors include:

CEP-1347

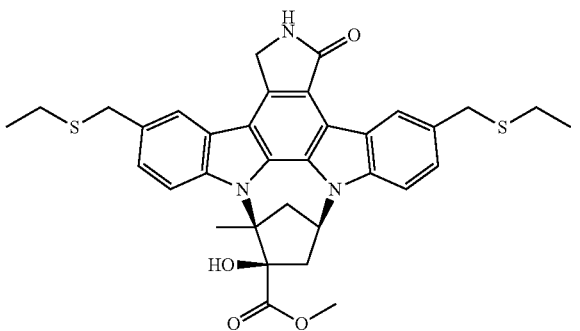

OSU-03012

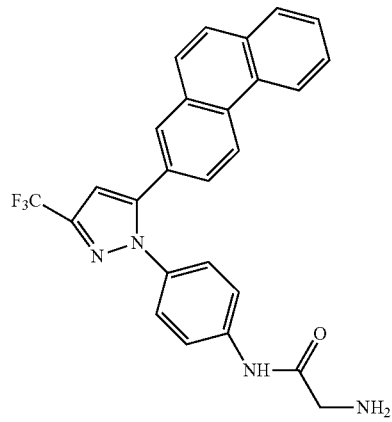

DW12

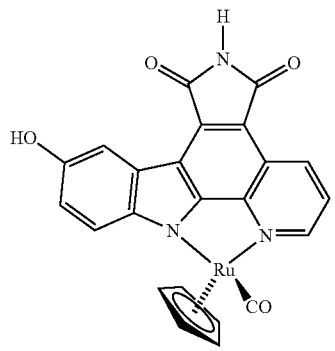

and in particular:

FL172

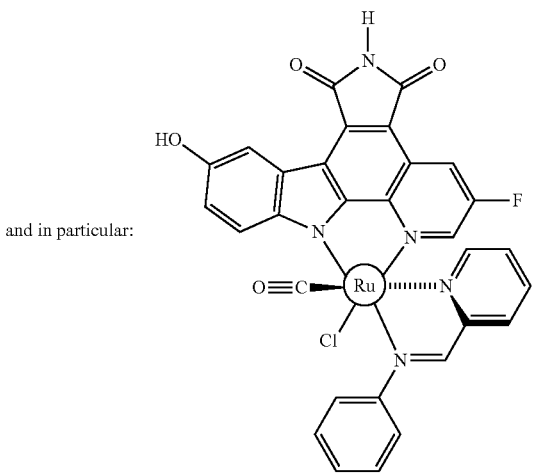

Other preferred PAK-Inhibitor are described in Nheu et al. 2002 (Cancer J 8 328-335), of which the disclosure is hereby incorporated by reference. These preferred PAK-Inhibitors include, CEP-1347, Staurosporine and:

ST-1347
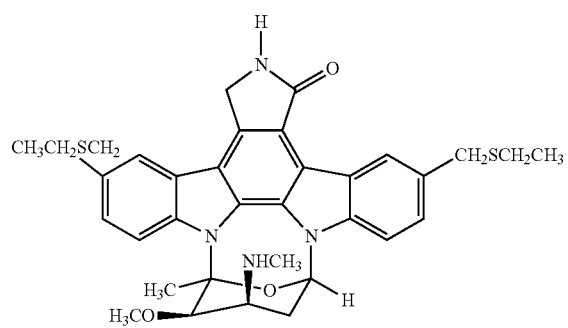
KT E496
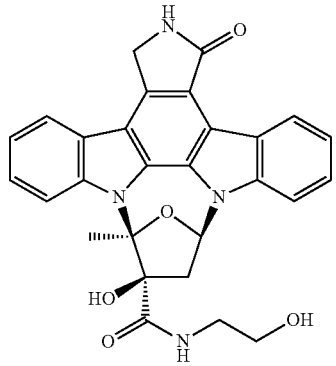
K252a
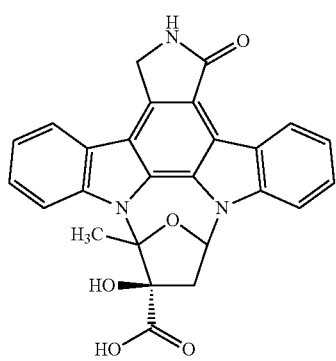
More preferred are dimers thereof, such as compounds having a general formula (V):
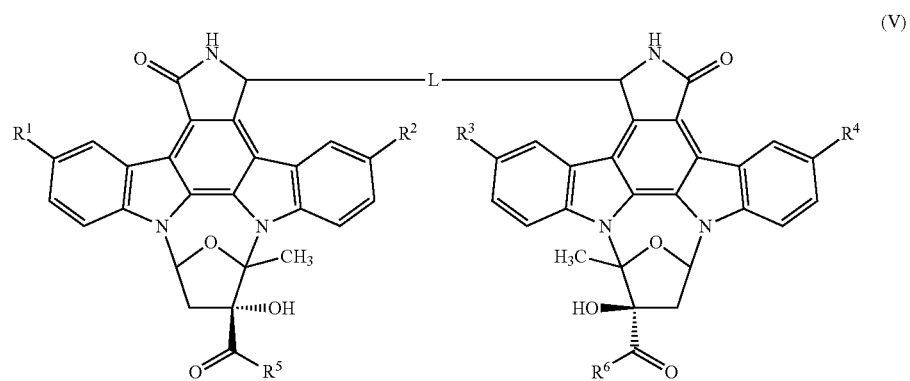
or having a general formula (VI):
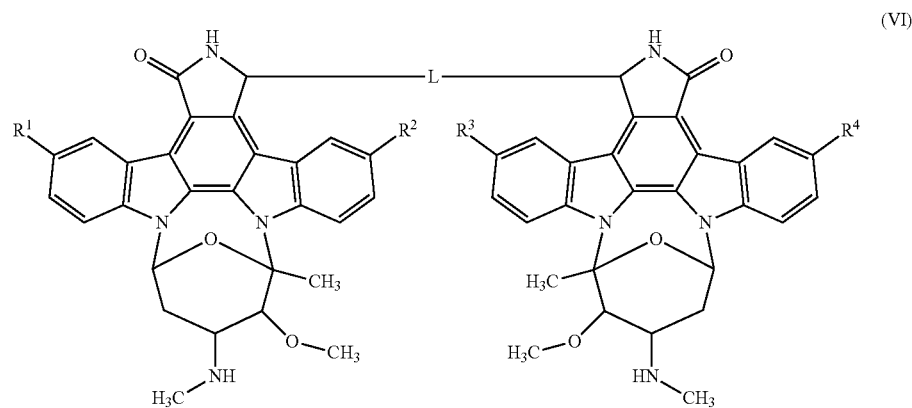

with L being a Linker selected from carbohydrate chains, that contain 5 to 9 C-atoms and optionally 1 to 3 hetero atoms (preferably selected from O, N and S). Preferred examples for Linkers are —$(CH_2)_n$- with n being integers ranging from 5 to 9, preferably 6 to 8 and —$CH_2$—O—$CH_2$—$CH_2$—O—$CH_2$—;

with $R^1$, $R^2$, $R^3$ and $R^4$ independently selected from H, C1 to C5-Alkyl and Alkyl containing Thiolor ether-bridges, in particular —$CH_2OCH_2CH_3$ and —$CH_2SCH_2CH_3$ and $R^5$ and $R^6$ selected from OH, Methoxy with C1 to C3 and —NH—$(CH_2)_m$-OH with m being integers ranging from 1 to 3, preferably OH or —NH—$CH_2$—$CH_2$—OH.

A preferred dimer is:

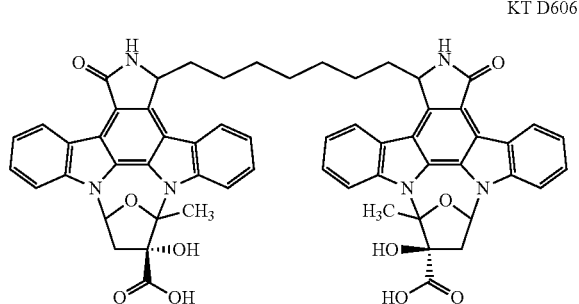 [SMILES: CC12OC(C[C@]1(O)C(=O)O)n1c3ccccc3c3c4c(c5c6ccccc6n2c5c31)C(CCCCCCCC1NC(=O)c2c1c1c3ccccc3n3c1c1c2c2ccccc2n1C1C[C@](O)(C(=O)O)C3(C)O1)NC4=O]

KT D606

Another preferred PAK-Inhibitor is:

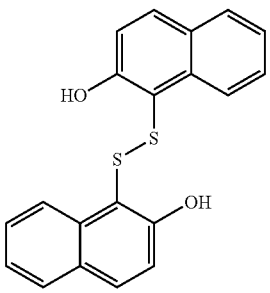 [SMILES: Oc1ccc2ccccc2c1SSc1c(O)ccc2ccccc12]

including its pharmaceutically acceptable salts and prodrugs. This PAK-Inhibitor is named IPA-3 (1,1'-Dithiodi-2-naphthol) and described by Deacon et al. 2008 Chem Biol. 15(4): 322-3, of which the disclosure is hereby incorporated by reference.

Further PAK-Inhibitors are selected from peptides inhibiting PAK1, PAK2 or PAK4, preferably including the Pak inhibitor domain (PID), preferably amino acids 83-149 in Pak 1.

Further PAK-Inhibitors are preferably chosen from small hairpin RNA (shRNA) and small interference RNA (siRNA) inhibiting PAK1, PAK2 or PAK4, most preferably chosen from RNA encoded by one of the following DNA sequences:

| SEQ ID | Sequence | Source (Genbank, NCBI) |
|---|---|---|
| 16 | TAACGGCCTAGACATTCAATT | Pr006097657.1 siRNA probe, sense strand |
| 17 | TTGAATGTCTAGGCCGTTATT | Pr006097657.1 siRNA probe, antisense strand |
| 18 | GGATGATGATGATGATGATTT | Pr006097658.1 siRNA probe, sense strand |
| 19 | ATCATCATCATCATCATCCTT | Pr006097658.1 siRNA probe, antisense strand |
| 20 | TGCTGTTGACAGTGAGCGAGGCCTAGACATTC AAGACAAATAGTGAAGCCACAGATGTATTTGT CTTGAATGTCTAGGCCGTGCCTACTGCCTCGGA | Pr144737.1 shRNA probe V2HS_152618 |
| 21 | TGCTGTTGACAGTGAGCGACCCAAGAAAGAGC TGATTATTTAGTGAAGCCACAGATGTAAATAA TCAGCTCTTTCTTGGGCTGCCTACTGCCTCGGA | Pr145555.1 shRNA probe V2HS_152621 |
| 22 | CCGGCCAAGAAAGAGCTGATTATTACTCGAGT AATAATCAGCTCTTTCTTGGTTTTT | Pr008643492.1 shRNA probe TRCN0000002224 |
| 23 | CCGGGTTCTGGATGTGTTGGAGTTTCTCGAGA AACTCCAACACATCCAGAACTTTTT | Pr008643493.1 shRNA probe TRCN0000010688 |
| 24 | CCGGCGATGAGAAATACCAGCACTACTCGAGT AGTGCTGGTATTTCTCATCGTTTTT | Pr008643494.1 shRNA probe TRCN0000002225 |
| 25 | CCGGGCGATCCTAAGAAGAAATATACTCGAGT ATATTCTTCTTAGGATCGCTTTTT | Pr008643495.1 shRNA probe TRCN0000002226 |
| 26 | CCGGCTTCTCCCATTTCCTGATCTACTCGAGTA GATCAGGAAATGGGAGAAGTTTTT | Pr008643496.1 shRNA probe TRCN0000002227 |
| 27 | TGCTGTTGACAGTGAGCGCCCTGGACAACTTC ATCAAGATTAGTGAAGCCACAGATGTAATCTT GATGAAGTTGTCCAGGTTGCCTACTGCCTCGG A | Pr169284.1 shRNA probe V2HS_197812 |

-continued

| SEQ ID | Sequence | Source (Genbank, NCBI) |
|---|---|---|
| 28 | TGCTGTTGACAGTGAGCGACCTCAAAGCCATG AAGATGATTAGTGAAGCCACAGATGTAATCAT CTTCATGGCTTTGAGGGTGCCTACTGCCTCGGA | Pr006067570.1 shRNA probe V2HS_197682 |
| 29 | ACTTCATCAAGATTGGCGAGTTCAAGAGACTC GCCAATCT TGATGAAGTTT | Pr006097010.1 shRNA probe |
| 30 | TGCTGTTGACAGTGAGCGCGCAATGAAGAGTA ACCGTTAATAGTGAAGCCACAGATGTATTAAC GGTTACTCTTCATTGCTTGCCTACTGCCTCGGA | Pr144543.1 shRNA probe V2HS_152629 | and complementary sequences thereof, as well as combinations of these RNA. The sequences 16-30 disclosed herein are the DNA-sequences for expressing the siRNA or shRNA.

An important element of this invention is that Rac/Pak dependent endocytosis is required for STAT6 activation in the Interleukin-4 and Interleukin-13 signaling pathway. In the state of the art it was believed that formation of a pentameric complex containing the ligand, the two receptor chains and the bound Janus kinases at the cytoplasmic receptor tails was sufficient for activation of STAT6. These complexes are supposed to form Rac/Pak at the plasma membrane in response to ligand binding. The inventors could detect ligand dependent formation of the type II complex (IL-13R) at the plasma membrane but, surprisingly, not of the type I complex (IL-4R). Whether the signaling complex is formed on the plasma membrane or not, STAT6 activation could be blocked by Rac/Pak specific endocytosis inhibitors.

According to this new model, endocytosis provides translocation of receptor bound ligand (IL-4 or IL-13) into a specific type of early sorting endosomes, where Stat6 activation takes place. The diameter of the compartment is up to 500 nm and thus clearly visible with a microscope. In contrast to other cytoplasmic vesicles, these endosomes appear immobilized within the actin cortex. In live cells, they can be observed. e.g. by time lapsed imaging for several minutes. The dependent endocytosis is constitutive such that IL-2Rg (or IL-13Ra1) and IL-4Ra are constantly shuttling from the plasma membrane into these compartments. While IL-2-Rg becomes enriched in these endosomes, IL-4Ra is constantly shuttling back to the plasma membrane (recycling), as reflected by the presence of the recycling regulator Rab11 on these endosomes in addition to the early sorting endosomal marker Rab5. Translocation of a labeled ligand of IL-4R (or IL-13R) or labeled receptor chains (in particular IL-4Ra or IL-13Ra1) into the signaling endosomes can be used as a readout to identify new compounds modulating IL-4 signaling.

In yet another aspect, the invention relates to a method for screening compounds that modulate Interleukin-4 or Interleukin-13 signaling comprising:
  a) contacting a cell that expresses Il-4R or IL-13R in the presence of Interleukin-4 or Interleukin-13 with a test compound;
  optional as a control: b) contacting a cell in the absence of Interleukin-4 and Interleukin-13 with the test compound; and
  c) determining the ability of the test compound to modulate Rac/Pak driven endocytosis of the Il-4R or IL-13R;
wherein the ability of the test compound to modulate Rac/Pak driven endocytosis of the Il-4R or IL-13R indicates modulation of Interleukin-4 and Interleukin-signaling, thereby identifying a compound which modulates Interleukin-4 and Interleukin-13 signaling. The cells expressing Il-4R or IL-13R can either be cells expressing the IL-4Ra as well as IL-2g and/or IL-13Ra1 endogenously or cells that are transfected to express these proteins. The term "transfection" includes transient transfection as well as stable transfections.

As described above, Rac/Pak driven endocytosis of the Il-4R or IL-13R is preferably detected by using a labeled ligand (IL-4 or IL-13), a labeled receptor chain (preferably IL-4Ra or IL-13Ra1) and/or receptor associated pathway component (such as JAK-1 or JAK-3) and detecting the label in endosomes.

Ligand, receptor chain or co-receptor components are preferably labeled with fluorescent dyes or fluorescent proteins. The ligand is preferably labeled with a fluorescent dye. Receptor chains and/or co-receptor are preferably labeled by linking them to a fluorescent protein (such as GFP) or another reporter protein (preferably an enzyme reporter such as luciferase or β-galactosidase) to obtain a fusion protein. Alternatively receptor chains and/or co-receptor can be tagged (e.g. with a His-tag or GST-tag) and the tag is subsequent detected with a labeled compound binding specific to the tag (such as labeled trisNTA binding to the His-tag) or anti-GST.

Preferably the ligand and at least one of the receptor chains or a co-receptor component (like JAK1 or JAK3) are labeled (with different labels) in order to detect co-localization in the endosomes. This assay can be used for a high content screen (HCS). The IL-4R and IL-13R internalization process bears beneficial features for HCS.

For example, the IL-4R processing endosomes are closely related to the surface plasma membrane and therefore be easily imaged close to the cover glass where the cells adhere. Therefore the z-position is accessible for automation. Also the particular endosomes can be highlighted by stably expressing a labeled receptor or co-receptor component, e.g. the GFP-tagged IL-2Rg or a GFP-tagged JAK3. Moreover, loading can be achieved with a labeled ligand targeting the IL-4R or IL-13R.

A two-color assay benefits from detecting the targeted endosomes on a background of various kinds of cytoplasmic compartments. As an optional additional readout the phosphorylation of Stat family transcription factors can be detected, e.g by using a Stat6-driven luciferase reporter.

The invention also comprises agents inhibiting Rac/Pak driven endocytosis for use for the treatment of conditions showing an excessive IL-4 and -13 signaling, in particular the inflammatory diseases associated with a deregulation of the immune system, such as asthma, and particularly the treatment of atopic dermatitis. The agents inhibiting Rac/Pak driven endocytosis that are preferably selected from agents inhibiting rac-1 or Pak1/2. More preferred are the agents inhibiting Rac/Pak driven endocytosis that are selected from the agents inhibiting Rac and PAK listed herein.

The invention also comprises the use of agents inhibiting Rac/Pak driven endocytosis for the manufacture of a medicament for the treatment of conditions showing an excessive IL-4 and -13 signaling, in particular the inflammatory diseases associated with a deregulation of the immune system, such as asthma, and particularly the treatment of atopic dermatitis. Again the agents inhibiting Rac/Pak driven endocytosis are preferably selected from agents inhibiting rac-1 or Pak1/2. More preferred are the agents inhibiting Rac/Pak driven endocytosis that are selected from the agents inhibiting Rac and PAK listed herein.

The methods for treatment include administering to a subject in need thereof, a pharmaceutical composition containing a therapeutically effective amount of an inhibitor of Rac/Pak driven endocytosis. In one aspect, in particular for the treatment of asthma, the composition is aerosolized prior to administration, and thus may be administered via inhalation once or twice per day. In another aspect, in particular for the treatment of atopic dermatitis, the composition is formulated for topical administration, e.g. as a cream, salve, lotion, gel or wax. The amounts of inhibitor of Rac/Pak driven endocytosis are preferably chosen in way that the local dose in the tissue (e.g. the lung or the skin) achieves a dose between 10 to 200 µmol/l, preferably 20 to 100 µmol/l. The dose in the pharmaceutical composition is preferably 50 µmol/l or higher, more preferred 100 µmol/l to 1 mmol/l. The subject may be a mammal, such as a human.

A pharmaceutical composition containing the inhibitor of Rac/Pak driven endocytosis of the invention typically contains a pharmaceutically acceptable carrier, such as saline. In other embodiments, the inhibitor of Rac/Pak driven endocytosis is conjugated to a polymer. Polymers useful in the invention include, but are not limited to, hydrophilic polymers, such as polyvinylpyrrolidone, and hydrophobic polymers, such as polyethylene glycol.

Although the invention describes various dosages, it will be understood by one skilled in the art that the specific dose level and frequency of dosage for any particular subject in need of treatment may be varied and will depend upon a variety of factors. These factors include the activity of the specific polypeptide or functional fragment thereof, the metabolic stability and length of action of that compound, the age, body weight, general health, sex, diet, mode and time of administration, rate of excretion, drug combination, the severity of the particular condition, and the host undergoing therapy. Generally, however, dosage will approximate that which is typical for known methods of administration of the specific compound.

Thus, a typical dosage of the inhibitor of Rac/Pak driven endocytosis will be about 0.1 to 1 mg/kg. For example, for administration of the inhibitor of Rac/Pak driven endocytosis, an approximate dosage by aerosol inhalation would be about 0.3 mg to 60 mg. Approximate dosages include, but are not limited to about 0.3 mg, about 0.5 mg, about 1.0 mg, about 3.0 mg, about 20 mg, about 30 mg or about 60 mg, to a subject, with dosages administered one or more times per day or week.

In another illustrative example, an approximate dosage for administration of the inhibitor of Rac/Pak driven endocytosis by subcutaneous injection includes, but is not limited to, about 25 mg. Treatment by administration of the inhibitor of Rac/Pak driven endocytosis may span days, weeks, years, or continue indefinitely, as symptoms persist. Hence, an appropriate dose and treatment regimen can be determined by one of ordinary skill in the art using routine procedures such as those provided herein.

The compositions and formulations of the invention can be administered systemically or locally. Local administration, preferably topically, inter alia as an aerosol, such as a nebulized inhalation spray or a dry powder aerosol to part of the subject's body in need of treatment is preferred. As used herein, "systemic administration" or "administered systemically" refers to compositions or formulations that are introduced into the blood stream of a subject, and travel throughout the body of the subject to reach the part of the subject's body in need of treatment at an effective dose before being degraded by metabolism and excreted. Systemic administration of compositions or formulations can be achieved, for example, by oral application (e.g., syrups, tablets, capsules and the like) and needle injection.

As used herein, "local administration" or "administered locally" refers to compositions or formulations that are introduced directly to part of the subject's body in need of treatment. Compositions or formulations can be delivered locally, for example, by injection (e.g., injection of anesthetic into a patient's gums) or topically (e.g., creams, ointments, and sprays). It should be understood that local administration can result in systemic levels of the composition or formulation following administration (e.g., an inhaled composition may result in systemic levels of the composition).

As used herein, the term "aerosol" refers to any gaseous suspension of fine solid or liquid particles. As such, the term "aerosolized" refers to being in the form of microscopic solid or liquid particles dispersed or suspended in air or gas. As used herein, the term "nebulize" refers to the act of converting (a liquid) to a line spray or atomizing. Accordingly, the term "dry powder aerosol" refers to any microscopic solid suspended in gas, typically air. It is also possible for the compositions of the invention to be formulated as a slow-release preparation. A short-term therapy or a continuous therapy is possible in the case of all the therapy forms.

Therapeutic formulations of the inhibitor of Rac/Pak driven endocytosis are prepared for administration and/or storage by mixing the inhibitor of Rac/Pak driven endocytosis, after achieving the desired degree of purity, with pharmaceutically and/or physiologically acceptable carriers, auxiliary substances or stabilizers (Remington's Pharmaceutical Sciences, loc. cit.) in the form of a lyophilisate or aqueous solutions. The term "pharmaceutically acceptable" or "physiologically acceptable," when used in reference to a carrier, is meant that the carrier, diluent or excipient must be compatible with the other ingredients of the formulation and not deleterious to the recipient thereof.

In general, the pharmaceutical compositions are prepared by uniformly and intimately bringing the active ingredient into association with a liquid carrier or a finely divided solid carrier or both, and then, if necessary, shaping the product into the desired formulation. Acceptable carriers, auxiliary substances or stabilizers are not toxic for the recipient at the dosages and concentrations employed; they include buffers such as phosphate, citrate, tris or sodium acetate and other organic acids; antioxidants such as ascorbic acid; low molecular weight polypeptides (less than approximately 10 residues), proteins such as serum albumin, gelatin or immunoglobulins; hydrophilic polymers such as polyvinylpyrrolidone; amino acids such as glycine, glutamine, asparagine, arginine, leucine or lysine; monosaccharides, disaccharides and other carbohydrates, for example glucose, sucrose, mannose, lactose, citrate, trehalose, maltodextrin or dextrin; chelating agents such as EDTA; sugar alcohols such as mannitol or sorbitol; salt-forming counter-ions such as sodium, and/or non-ionic surface-active substances such as Tween, Pluronics or polyethylene glycol (PEG).

Such pharmaceutical compositions may further contain one or more diluents, fillers, binders, and other excipients, depending on the administration mode and dosage form contemplated. Examples of therapeutically inert inorganic or organic carriers known to those skilled in the art include, but are not limited to, lactose, corn starch or derivatives thereof, talc, vegetable oils, waxes, fats, polyols such as polyethylene glycol, water, saccharose, alcohols, glycerin and the like. Various preservatives, emulsifiers, dispersants, flavorants, wetting agents, antioxidants, sweeteners, colorants, stabilizers, salts, buffers and the like can also be added, as required to assist in the stabilization of the formulation or to assist in increasing bioavailability of the active ingredient(s) or to yield a formulation of acceptable flavor or odor in the case of oral dosing. The inhibitor of Rac/Pak driven endocytosis can be administered alone, or in various combinations, and in combination with other therapeutic agents.

The inhibitor of Rac/Pak driven endocytosis used in the invention is normally stored in lyophilized form or in solution. The inhibitors of Rac/Pak driven endocytosis used in the invention are typically water soluble and available as a dry solid to be administered as a dry powder, or reconstituted in a the pharmaceutical compositions as described herein.

The present invention is not limited to the particular methodology, protocols, cell lines, vectors, reagents, etc., described herein, as these may vary. It is also to be understood that the terminology used herein is used for the purpose of describing particular embodiments only, and is not intended to limit the scope of the present invention. As used herein and in the appended claims, the singular forms "a," "an," and "the" include plural reference unless the context clearly dictates otherwise.

The following examples are intended to illustrate but not limit the invention.

EXAMPLE 1

Effect of Inhibitors of Rac/Pak Driven Endocytosis on IL-4/IL-13 Signaling in Epithelial Cells (Type II Signaling)

Figure 1:
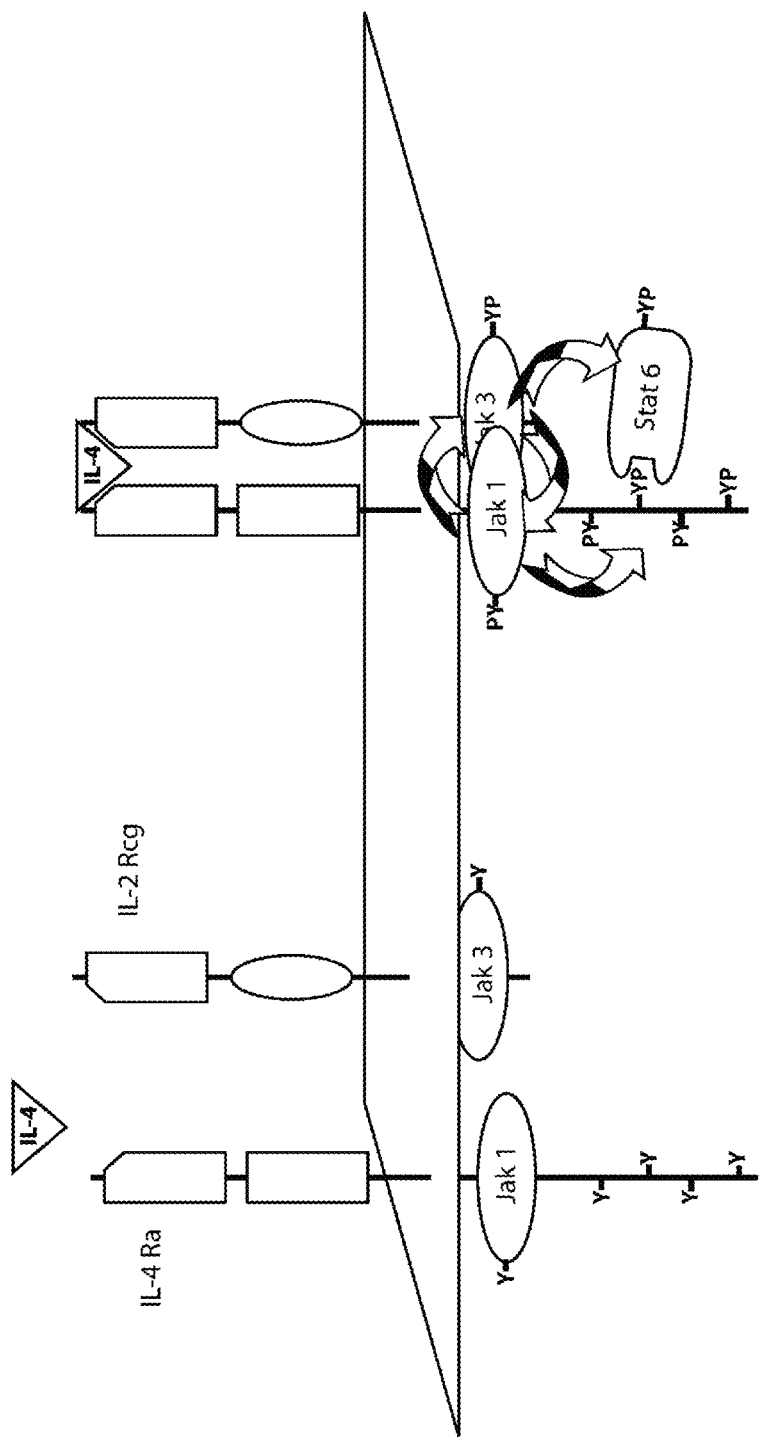
FIG. 1 is a graphical representation showing the present text book view of Il-4 signaling.
Figure 2:
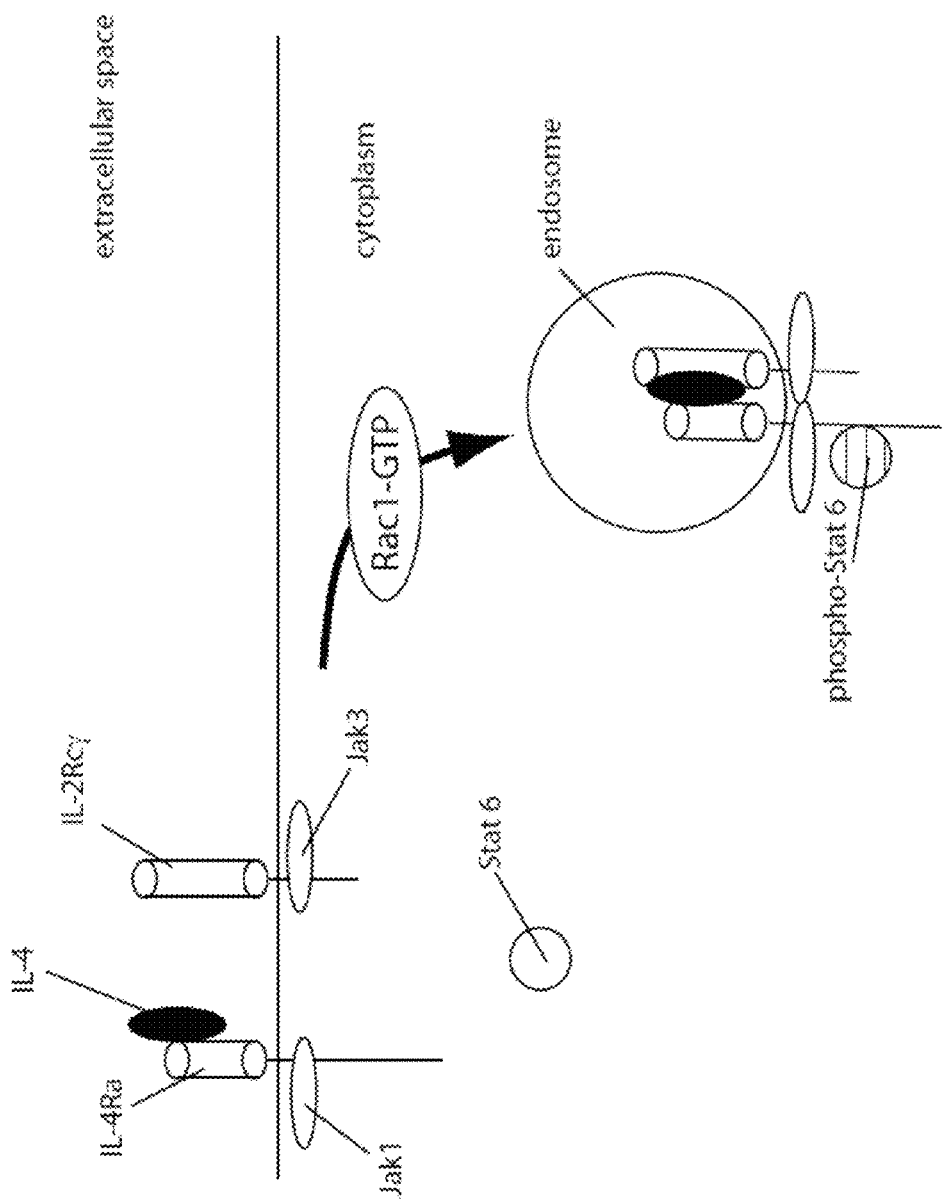
FIG. 2 is a graphical representation showing the view of Il-4 signaling according to the invention.
Figure 3:
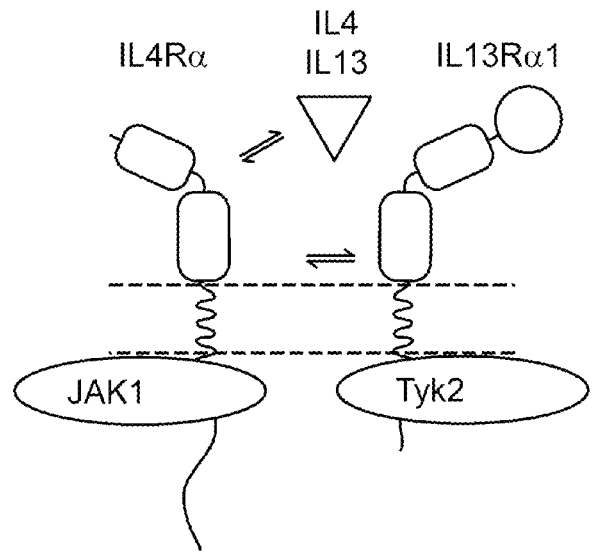
FIG. 3 is a graphical representation showing the association of the IL-4 receptor alpha chain (IL-4Ra) with JAK1 and the association of the IL-13 receptor alpha chain (IL-13Ra1) with Tyk2.
Figure 4:
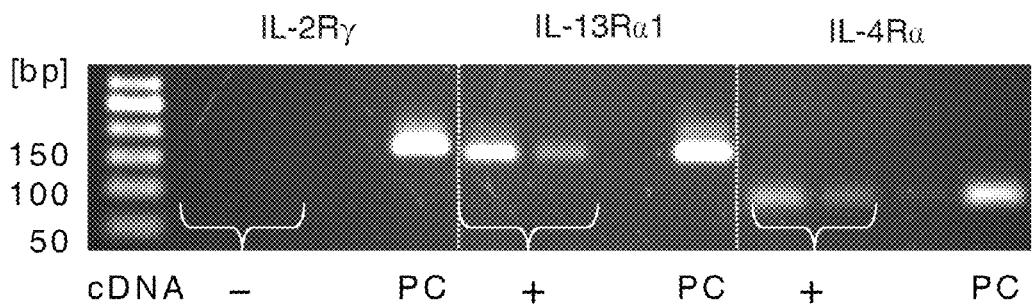
FIG. 4 shows that the components of endogenous IL-4R type II signaling IL-13Ra1 (IL-13Ra1) and IL-4Ra (IL-4Ra) are present in epithelial HEK293T cells at the messenger RNA level, whereas the type I specific IL-2Rg (IL-2Rγ) is absent. All primer pairs were validated with a plasmid encoding the respective gene as a positive control (PC).
Figure 5:
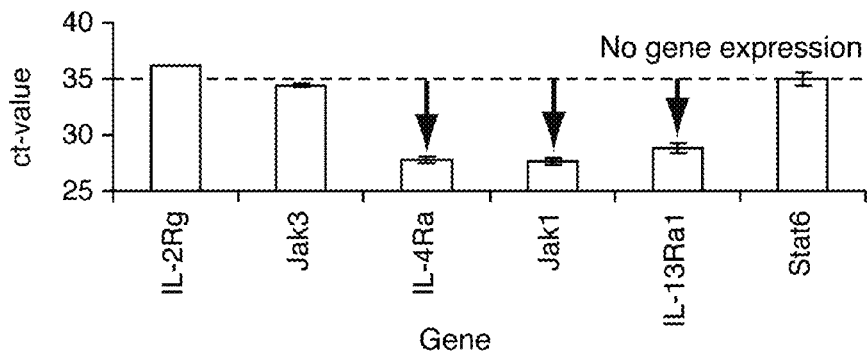
FIG. 5 Quantitative RT-PCR shows that the components of endogenous IL-4R type II signaling IL-13Ra1, IL-4Ra and Jak I are present in epithelial HEK293T cells at the messenger RNA level (low ct-value), while Stat6 and the type I specific components, IL-2Rg and Jak3 were absent (high ct-value).
Figure 6:
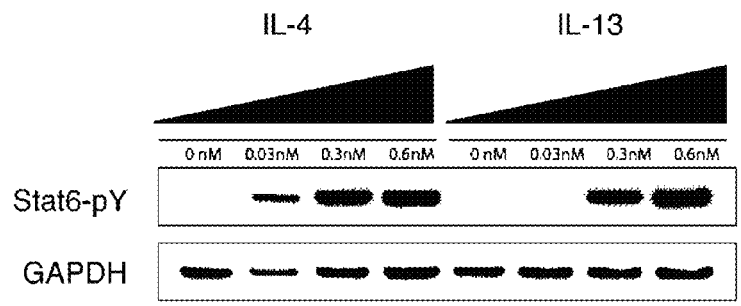
FIG. 6 shows the results of HEK293T cells transfected with Stat6 and stimulated with either IL-4 or IL-13, phosphorylated Stat6 became detectable by immunoblotting.
Figure 7:
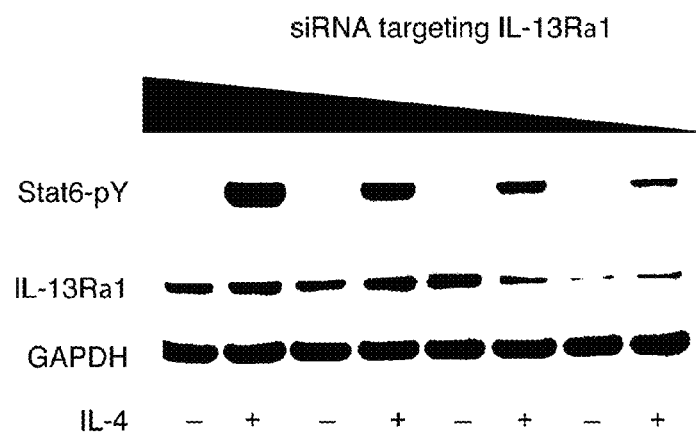
FIG. 7 shows the results of HEK293T cells transfected with Stat6 and stimulated with IL-4. Co-transfected RNAi mediated knockdown of the endogenous Il-13Ra1 reduces Stat6 phosphorylation, showing that signaling activity was mediated by IL-13Ra1 (type II pathway).
Figure 8:
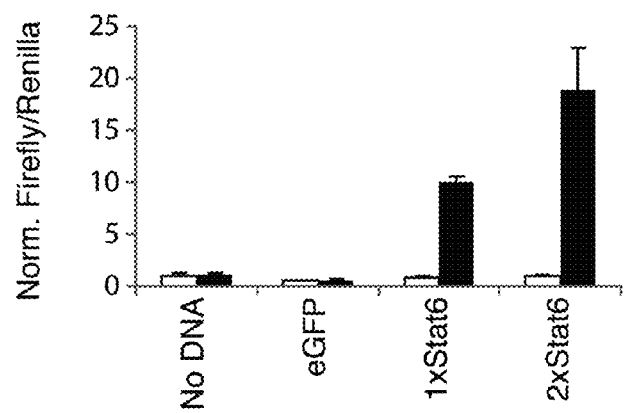
FIG. 8 shows results on that HEK293T cells transfected with a Stat6-driven luciferase reporter (1× Stat6) or co-transfected with the Stat6-plasmid used in all other experiments (2× Stat6), showing that Stat6 transfection is results in functional Stat6.

It was verified by RT-PCR that HEK293T (human epithelial cell line—ATCC number CRL-11268) cells expressed the endogenous type II IL-4 pathway components IL4-Ra, IL-13Ra1, Jak1, while Stat6 and the type I specific components IL-2Rg, and Jak3 were absent (FIG. 4 and FIG. 5). In HEK cells ectopically expressing human Stat6 under the cytomegalovirus promoter (pcDNA3.1-GS-Stat6, Gene Storm, Invitrogen) and stimulated with either IL-4 or IL-13, phosphorylated Stat6 became detectable by immunoblotting (FIG. 6). Co-transfected RNAi (Sigma Aldrich, #EHU-029151) mediated knockdown of the endogenous IL-13Ra1 subunit verified that this signaling activity was mediated by the type II receptor pathway (FIG. 7). Ectopically Stat6 is functional. Co-transfection with a Stat6-driven luciferase reporter (Promega dual luciferase reporter assay using the reporter plasmids pTKLuc-3×STAT6-RE/pRTLK) was IL-4 dependent and scaled with the amount of ectopically expressed Stat6 (pcDNA3.1-GS-Stat6) while expressing GFP from pEGFP-N1 showed no response (FIG. 8).

To test whether IL-4 signaling depends on compounds inhibiting Rac/Pak dependent endocytosis, HEK293T cells were transfected with a plasmid encoding human Stat6. Following transfection, cells were grown overnight, treated with inhibitors and/or ligands, lysed, proteins separated electrophoretically under denaturing conditions, and phosphorylation of Stat6 detected by quantitative immunoblotting (Antibodies from Santa Cruz, anti-STAT6 (M-20) #sc-981 and anti-phospho-STAT6 (py641.18, #sc-136019; FIG. 9).

If not indicated otherwise, human recombinant IL-4 (Invitrogen, #PHC0045) was used at 3 ng/ml, and human recombinant IL-13 (Cell Signaling, #8905) was used at 10 ng/ml.

If not indicated otherwise, the dynamin inhibitor Dynasore (Sigma Aldrich, #D7693) was used at 320 µmol/l, the Rac1 inhibitor EHT-1864 (Sigma Aldrich, 41E-1657) at 50 µmol/l, and the PAK inhibitor IPA-3 (Sigma Aldrich, #I-2285) at 10 µmol/l. All three compounds reduced the Stat6 phosphorylation level (FIG. 9), indicating that the type II IL-4 signaling output depends on Rac/Pak dependent endocytosis.

EXAMPLE 2

Effect of Inhibitors of Rac/Pak Driven Endocytosis on Type I IL-4 Signaling

In a second series of experiments the inventors assayed the type I IL-4R. The pStat6 levels were determined under the following conditions:
  without ligand stimulation
  incubation with IL-4 ligand for 30 min
  10 min pre-incubation with inhibitor plus 30 min incubation with ligand and inhibitor
  40 min pre-incubation with inhibitor followed by removal of the inhibitor and 30 min incubation with ligand (washout).

To assay endogenous type I signaling was analyzed in the Jurkat T lymphocytic leukemia cell line (ATCC TIB 152) showing a specific sensitivity to Rac/Pak dependent endocytosis. Again, signaling was significantly reduced in the presence of Dynasore, EHT-1864, and IPA-3, while 2.8 µmol/l chlorpromazine (Sigma Aldrich, #C8138) had no effect (FIG. 13).

Figure 10:
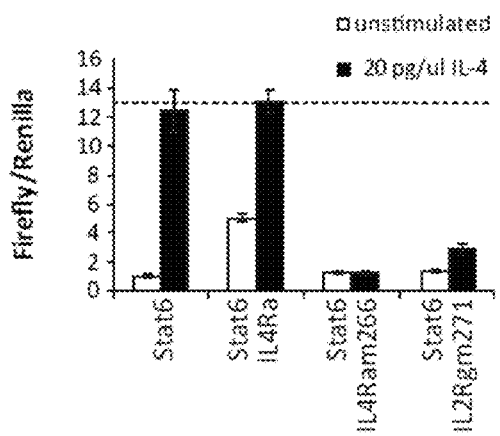
FIG. 10 shows IL-4 signaling in HEK293T cells reconstituted in HEK293T with receptor subunits for type I and type II IL-4R by a Stat6-responsive Luciferase assay. Endogenous components (type II) induced an IL-4 dependent signal (about 10 fold), when supplementing Stat6 and the luciferase reporter. Additional transfection of IL-4R alpha chain raised the baseline without further increase of the IL-4 dependent signal. In contrast, cytoplasmic truncated receptor (IL-4Ram266) and co-receptor (IL-2Rgm271) efficiently outcompeted the endogenous receptor components.
Figure 11:
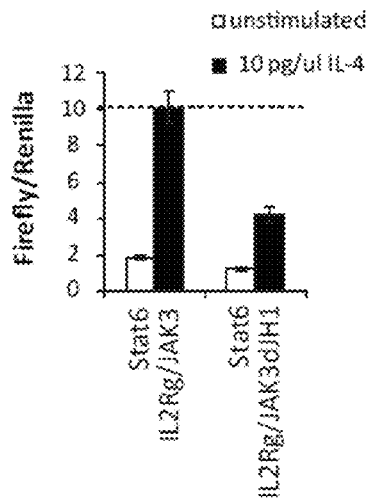
FIG. 11 shows that signaling can be reprogrammed to type I by supplementing full length IL-2Rg and JAK3. Accordingly, using a JAK3 lacking the kinase domain (JAK3dJH1) reduced the IL-4 dependent signal.
Figure 12:
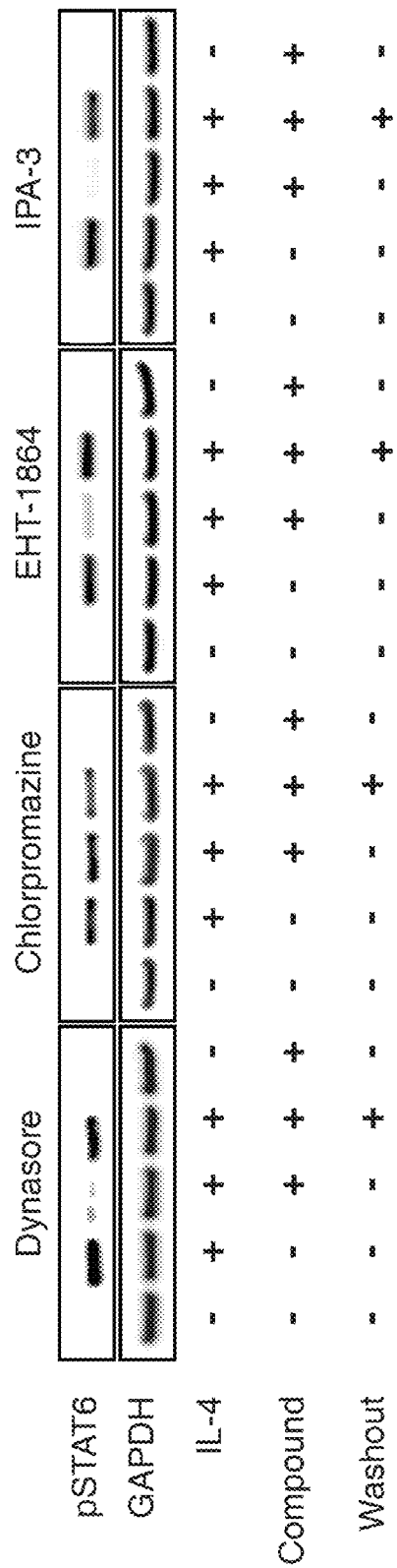
FIG. 12 shows the effect of the inhibitors Dynasore, as well as EHT-1864 and IP-3 on endogenous IL-4 signaling in lymphoid Jurkat cells transfected with Stat6. Chlorpromazine, which inhibits clathrin-dependent endocytosis, showed no inhibitory effect.

Then the inventors reconstituted a type I IL-4R in HEK293T by ectopically overexpressing the co-receptor subunits IL-2Rg (pIL2Rg-N) and Jak3 (pJAK3-EGFP-N1). Stimulating the cells with IL-4 in the presence and absence of inhibitors reproduced the same band pattern of Stat6-phosphorylation (FIG. 12). To verify that this signaling activity was largely mediated by the type I co-receptor IL-2Rg/Jak3 the inventors investigated dominant negative mutants with the STAT6 dependent dual luciferase reporter gene assay: in the type I overexpression state, IL-4 signaling was significantly reduced when using either IL-2Rg lacking the cytoplasmic tail (pIL2Rgm271-EGFP-N1) or Jak3, lacking the kinase domain (pJAK3dJH1-EGFP) (FIG. 10 and FIG. 11).

In summary, treatment with inhibitors indicated that the signaling dependent on Rac/Pak mediated endocytosis for both types of IL-4 receptors. Importantly, all these treatments were completely reversible, and cells regained their signaling competence after removal of the drugs by washing the cells with culture media (compound washout FIG. 12 and FIG. 13).

EXAMPLE 3

Figure 14:
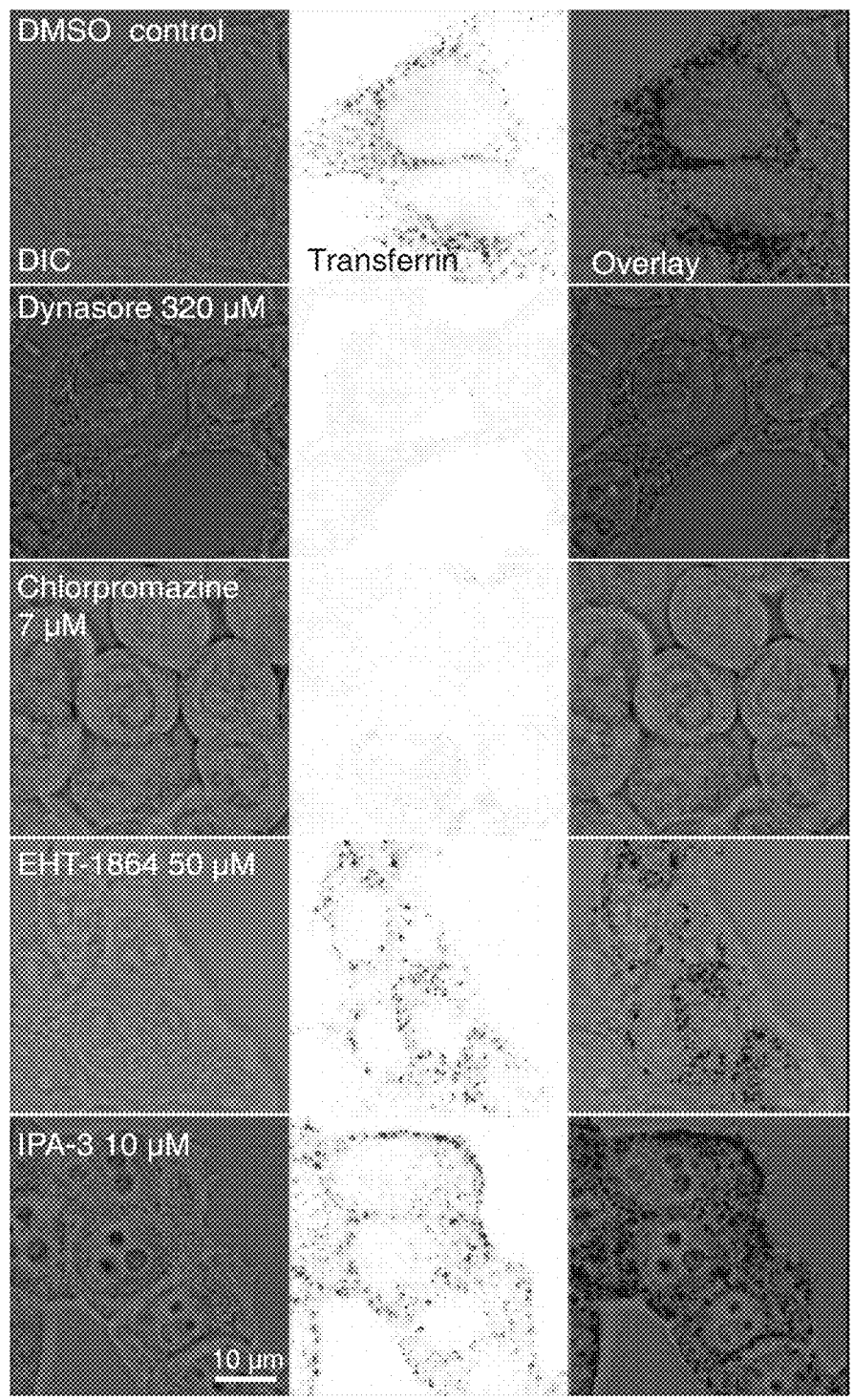
FIG. 14 shows the effect of the inhibitors on transferrin uptake in HEK cells (expressing endogenous transferrin receptor). DIC=differential interference contrast. Rac/Pak targeting inhibitors EHT-1864 as well as IP-3 have no effect on transferrin uptake; the cells are indistinguishable from a DMSO control. As expected, compounds targeting clathrin-dependent endocytosis like Dynasore and Chlorpromazine inhibit transferrin uptake.

Effect of Inhibitors on Rac/Pak Driven Endocytosis by Measuring Transferrin Uptake The inventors verified that the used compounds at the working concentration indeed blocked endocytosis by monitoring the uptake of 25 µg/ml fluorescent transferrin (Alexa568-transferrin, Invitrogen) with confocal fluorescence microscopy (FIG. 14). The experiment was performed with (untransformed) HEK-cells expressing endogenous transferrin receptor. As expected, dynamin dependent endocytosis could be blocked with Dynasore. Dynasore concentrations that blocked transferrin endocytosis (320 µmol/l) also prevented Stat6 phosphorylation in response to IL-4 and IL-13 stimulation. In contrast, treatment with chlorpromazine blocked transferrin uptake but not IL-4 signaling, excluding an involvement of the clathrin dependent endocytic machinery. As expected, inhibiting Rac1 and Pak 1/2 dependent actin polymerization by EHT-1864 and IPA-3 had no effect on transferrin uptake (FIG. 14).

Thus, the results demonstrate that both type I IL-4 signaling (via a complex involving IL-4, IL-4Ra, and IL-2Rg) and type 11 signaling (involving IL-4Ra and IL-13Ra I bound to either IL-4 or IL-13 require an essential endocytosis step before the signal can be transduced to the downstream transcription factor Stat6. Since many existing drug families target endocytosis of pathogen or host proteins this observation provides a promising new approach for the suppression of pathologically increased IL-4 and IL-13 receptor activation. In summary, the results provides evidence that IL-4 and IL-13 signaling require endocytosis by a clathrin independent endocytosis pathway that is dynamin dependent and driven by Rac and PAK.

Figure 15:
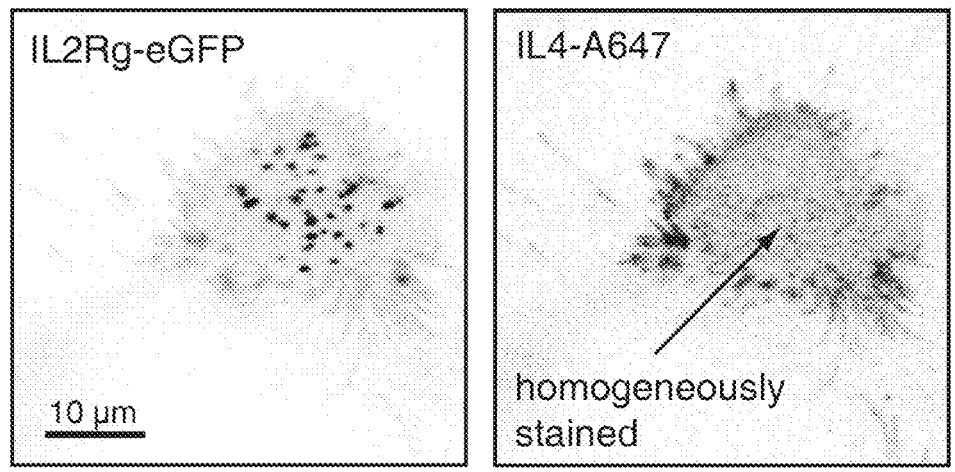
FIGS. 15 to 19 show the results of an assay to measure the kinetics of fluorescently, Alexa647 (Invitrogen) labeled IL-4 ligand, shuttling from the plasma membrane to the intracellular signaling compartment.

An important element of this invention is that Rac/Pak dependent endocytosis is required for STATE activation in the Interleukin-4 and Interleukin-13 signaling pathway. According to this new model, endocytosis provides translocation of receptor bound ligand (IL-4 or IL-13) into a specific type of early sorting endosomes, where Stat6 activation takes place. The diameter of the compartment is up to 500 nm and thus clearly visible with a confocal microscope. Fluorescently labeled compartments can be easily generated by expressing a fluorescently tagged IL-2Rg/JAK3 pair. Here the inventors used pIL2Rg-eGFP to stain the compartments in the GFP-channel (FIG. 15). In contrast to other cytoplasmic vesicles, these endosomes appear immobilized within the actin cortex. In live cells, they can be observed by time lapsed imaging for several minutes (compare GFP-channel of FIG. 15 and FIG. 16). The Rac/Pak dependent endocytosis is constitutive such that IL-2Rg and IL-4Ra are constantly shuttling from the plasma membrane into these compartments. IL-4Ra is probably shuttling back to the plasma membrane (recycling) as indicated by Rab11 positive endosomes. Thus, translocation of any fluorescent ligand of IL-4R into the signaling early sorting endosomes can be used as a readout to identify new compounds modulating IL-4 signaling.

EXAMPLE 4

Detection of Translocation of Labeled IL-4

The inventors created a fluorescently labeled IL-4 ligand (Alexa647—succinimidylester, Invitrogen)—further referred to as IL4-A647.

HEK293T were transfected with IL-4Ra, IL-2Rg-eGFP, and JAK3 as described above and cultured under standard culture conditions. The cells were incubated at 4° C. with the inhibitor (optional) and stained with 50 nmol/I IL4-A647 and washed with medium (DMEM without phenole red). The temperature release from 0° C. to 20° C. was defined as a reference point for the onset of endocytosis. Thenceforth, co-localization of eGFP with A647 was measured.

Figure 16:
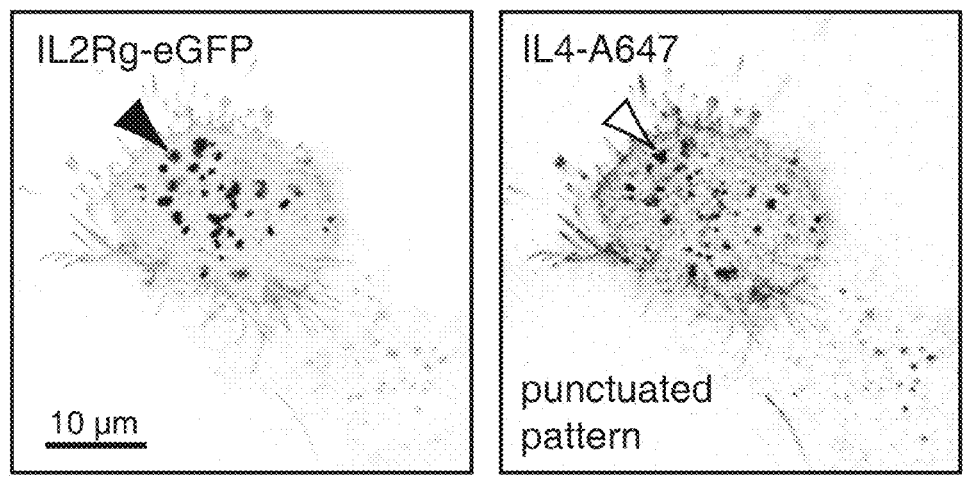
Figure 17:
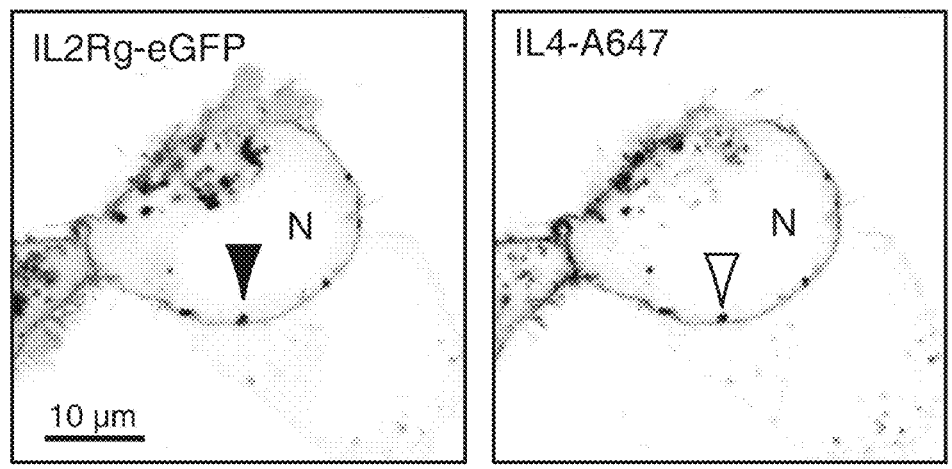
Figure 18:
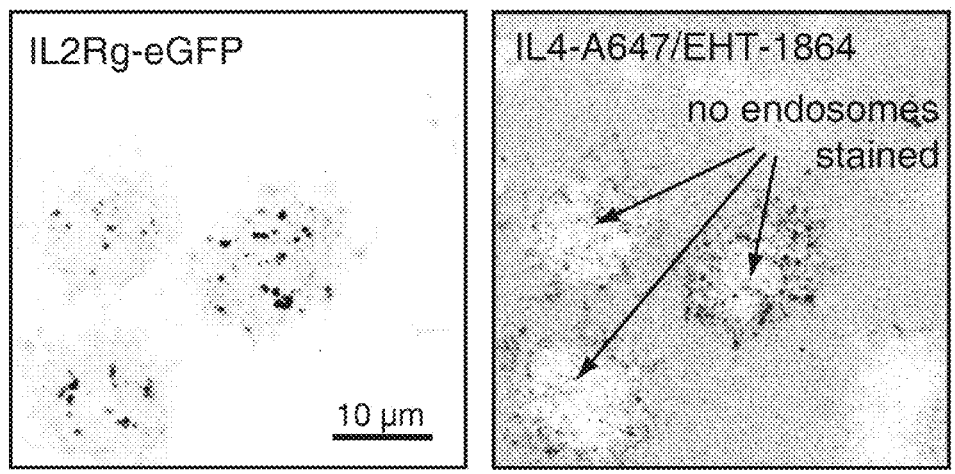
Figure 19:
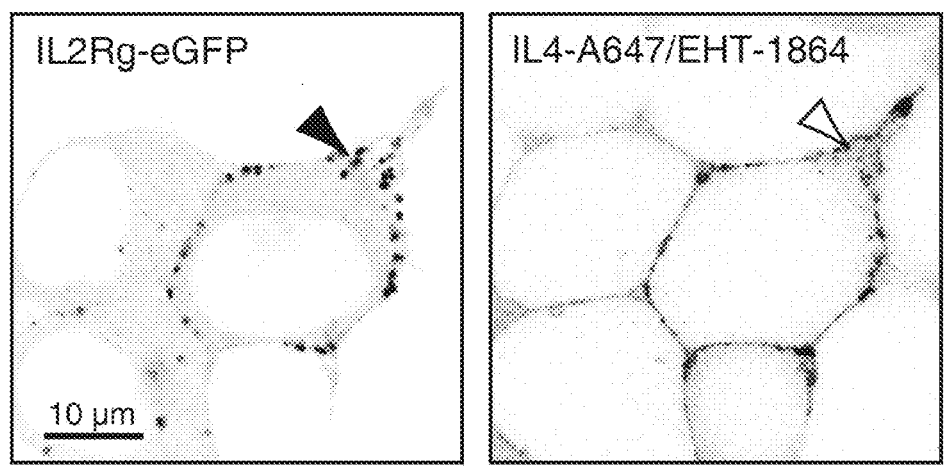

Applying the fluorescent IL-4-A647 under conditions in which endocytosis is suppressed (4° C.) allows to observe the kinetics of the translocation into the signaling endosomes. The endocytosis starts with a temperature release. FIG. 15 illustrates that in an initial state (timepoint 0 min, IL4-A647 channel) the plasma membrane of the IL-4Ra chain expressing cells is homogeneously stained. However, after several minutes, the A647 fluorescence a punctuated pattern appears in the IL4-A647 channel showing a high degree of colocalization to the GFP channel (FIG. 16). Association of the stained endosomes with the actin cortex and the plasma membrane is apparent in central confocal cross-sections through a central part of the cell (FIG. 17). As a proof-of-principle, pre-incubation of the cells with 50 µmol/l EHT-1864 reduced significantly the loading of the signaling endosome with IL4-A647 for up to 20 minutes (FIG. 18). Such a readout could therefore be used to detect IL-4 translocation inhibitors.

High content screening is based on imaging of formaldehyde fixed adherent cell populations with multiple fluorescence color channels. In the literature, HCS in the context of endocytosis is still cutting edge and mainly applied in the field of GPCR signaling. GPCRs for example, show fast internalization upon ligand binding. Residence times of the complex at the plasma membrane range between several seconds to minutes.

A major issue in screening endocytosis events is the continuous maturation of endosomes leading to multiple shapes and sizes within a cell. Thus, it is difficult to design image evaluation algorithms sufficiently robust for detection of a targeted subset of endosomes. Here, we think our IL-4R internalization process bears beneficial features. (1.) The IL-4R processing endosomes are closely associated with the surface plasma membrane and therefore be easily imaged close to the cover glass where the cells adhere. Therefore the z-position is accessible for automation (2.) The particular endosomes can be highlighted by stably expressing a fluorescent co-receptor component, either the GFP-tagged IL-2Rγ or a GFP-tagged JAK3. (3.) Loading can be achieved with any fluorescent ligand of orthogonal color targeting the IL-4R. So far we tested A647-labeled IL-4, and A647-labeled trisNTA binding to hexahistidine stretch at the N-terminus of IL-4Rα. A two-color assay benefits from detecting the targeted endosomes on a background of various kinds of cytoplasmic compartments.

The invention claimed is:

1. A method for reducing Interleukin-4 (IL-4R) or Interleukin-13 (IL-13R) signaling in a cell or subject comprising administering an inhibitor of Rac/Pak driven endocytosis in an amount sufficient to reduce or inhibit endocytosis of IL-4R or IL-13R, wherein, the IL-4R or IL-13R signaling is associated with Rac/Pak driven endocytosis.

2. The method of claim 1, wherein said inhibitor of Rac/Pak driven endocytosis is administered in amount effective to reduce or inhibit phosphorylation of Stat family transcription factors.

3. The method of claim 1, wherein the inhibitor of Rac/Pak driven endocytosis is selected from agents inhibiting Rac-1 or Pak1/2.

4. The method of claim 1 or 2, wherein the inhibitor is selected from the group consisting of peptides inhibiting Rac-1,

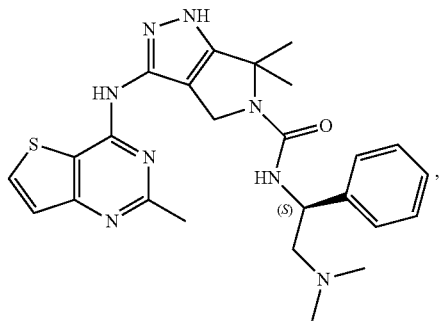

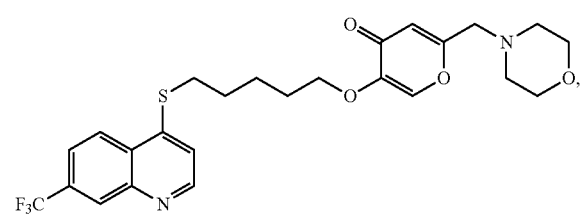

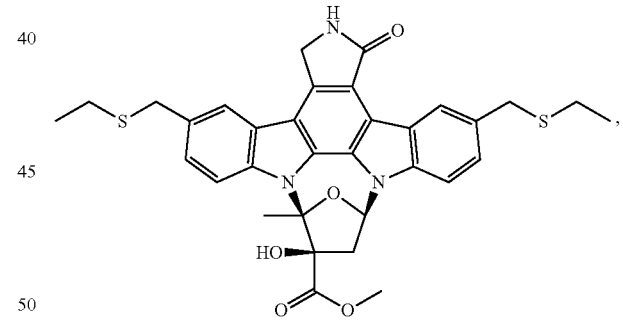

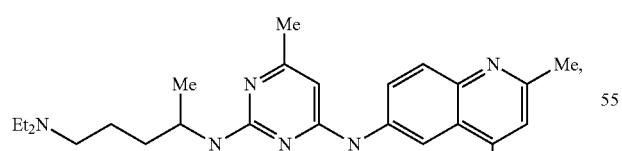

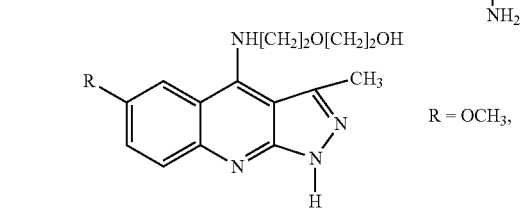

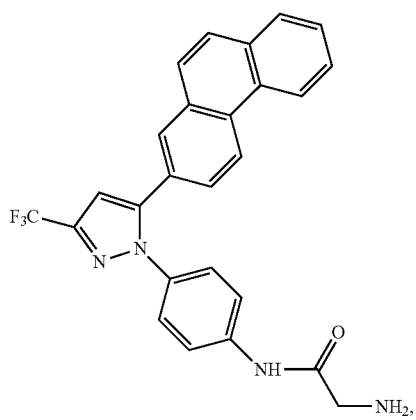

-continued

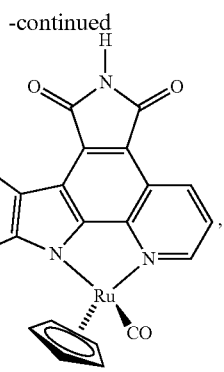

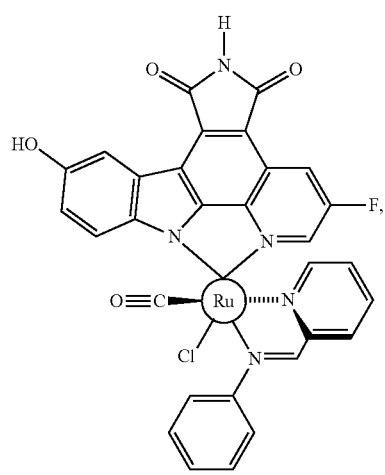

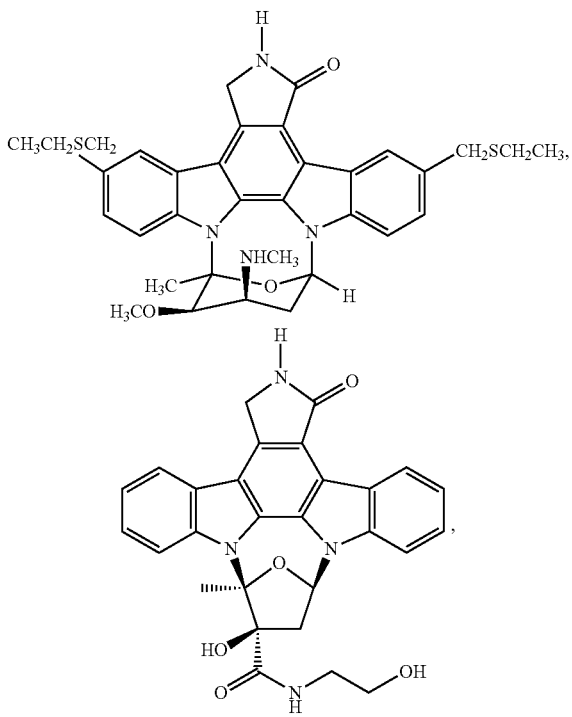

-continued

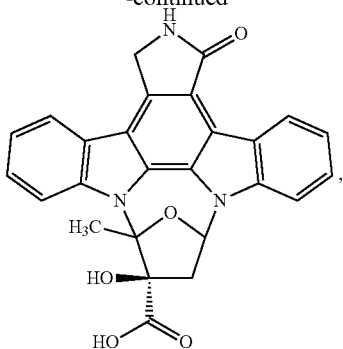

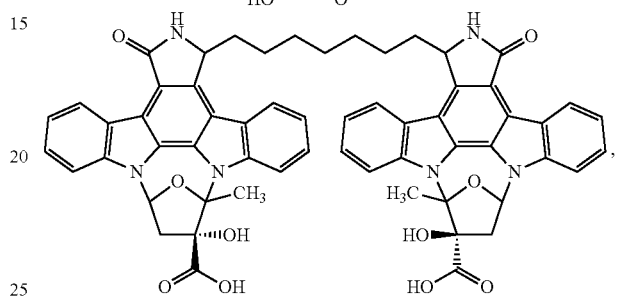

peptides inhibiting PAK1, PAK2 or PAK4 including the Pak inhibitor domain (PID), small hairpin RNA (shRNA), small interference RNA (siRNA) inhibiting Rac1, PAK1, PAK2 and PAK4, and combinations thereof.

5. The method of claim 4, wherein said peptide inhibiting Rac-1 is N17Rac.

6. The method of claim 4, wherein said peptide inhibiting PAK1 comprises amino acids 83-149 of PAK1.

7. A method of treating a condition characterized by increased Interleukin-4 (IL-4R) or Interleukin-13 (IL-13R) levels in a subject in need thereof comprising administering an inhibitor of Rac/Pak driven endocytosis in a therapeutically effective amount, wherein, the increase in IL-4R or IL-13R levels is associated with Rac/Pak driven endocytosis.

8. The method of claim 7, wherein the inhibitor of Rac/Pak driven endocytosis is selected from agents inhibiting Rac-1 or Pak1/2.

9. The method of claim 8, wherein the inhibitor is selected from inhibitors as defined in claim 4.

10. The method of claim 7, wherein the condition characterized by increased Interleukin-4 or Interleukin-13 levels is selected from the group consisting of inflammatory conditions, asthma bronchiale, atopic dermatitis, and allergies, atopic syndromes, allergic rhinitis, th2-induced conditions, and combinations thereof.

11. A method of treating atopic dermatitis in a subject in need thereof comprising administering an inhibitor of Rac/Pak driven endocytosis in a therapeutically effective amount, wherein, the atopic dermatitis is associated with Rak/Pak driven endocytosis.

12. The method of claim 11, wherein the inhibitor of Rac/Pak driven endocytosis is selected from agents inhibiting rac-1 or Pak1/2.

13. The method of claim 11, wherein the inhibitor is selected from inhibitors as defined in claim 4.

* * * * *

SEQUENCE LISTING

<160> NUMBER OF SEQ ID NOS: 30

<210> SEQ ID NO 1
<211> LENGTH: 21
<212> TYPE: DNA
<213> ORGANISM: artificial sequences
<220> FEATURE:
<221> NAME/KEY: source
<222> LOCATION: 1..21
<223> OTHER INFORMATION: /mol_type="DNA"
    /note="DNA for siRNA Probe, sense strand"

/organism="artificial sequences"

<400> SEQUENCE: 1
caccactgtc ccaacactct t                                              21

<210> SEQ ID NO 2
<211> LENGTH: 21
<212> TYPE: DNA
<213> ORGANISM: artificial sequences
<220> FEATURE:
<221> NAME/KEY: source
<222> LOCATION: 1..21
<223> OTHER INFORMATION: /mol_type="DNA"
      /note="DNA for siRNA Probe, antisense strand"
      /organism="artificial sequences"

<400> SEQUENCE: 2
gagtgttggg acagtggtgt t                                              21

<210> SEQ ID NO 3
<211> LENGTH: 21
<212> TYPE: DNA
<213> ORGANISM: artificial sequences
<220> FEATURE:
<221> NAME/KEY: source
<222> LOCATION: 1..21
<223> OTHER INFORMATION: /mol_type="DNA"
      /note="DNA for siRNA probe , sense strand"
      /organism="artificial sequences"

<400> SEQUENCE: 3
ggagattggt gctgtaaaat t                                              21

<210> SEQ ID NO 4
<211> LENGTH: 21
<212> TYPE: DNA
<213> ORGANISM: artificial sequences
<220> FEATURE:
<221> NAME/KEY: source
<222> LOCATION: 1..21
<223> OTHER INFORMATION: /mol_type="DNA"
      /note="DNA for siRNA probe , antisense strand"
      /organism="artificial sequences"

<400> SEQUENCE: 4
ttttacagca ccaatctcct t                                              21

<210> SEQ ID NO 5
<211> LENGTH: 21
<212> TYPE: DNA
<213> ORGANISM: artificial sequences
<220> FEATURE:
<221> NAME/KEY: source
<222> LOCATION: 1..21
<223> OTHER INFORMATION: /mol_type="DNA"
      /note="DNA for siRNA probe , sense strand"
      /organism="artificial sequences"

<400> SEQUENCE: 5
cctttgtacg ctttgctcat t                                              21

<210> SEQ ID NO 6
<211> LENGTH: 21
<212> TYPE: DNA
<213> ORGANISM: artificial sequences
<220> FEATURE:
<221> NAME/KEY: source
<222> LOCATION: 1..21
<223> OTHER INFORMATION: /mol_type="DNA"

/note="DNA for siRNA probe , antisense strand"
/organism="artificial sequences"

<400> SEQUENCE: 6
tgagcaaagc gtacaaaggt t                                              21

<210> SEQ ID NO 7
<211> LENGTH: 97
<212> TYPE: DNA
<213> ORGANISM: artificial sequences
<220> FEATURE:
<221> NAME/KEY: source
<222> LOCATION: 1..97
<223> OTHER INFORMATION: /mol_type="DNA"
      /note="DNA for shRNA probe"
      /organism="artificial sequences"

<400> SEQUENCE: 7
tgctgttgac agtgagcgac gacactgtca cttgaccaat tagtgaagcc acagatgtaa    60
ttggtcaagt gacagtgtcg gtgcctactg cctcgga                             97

<210> SEQ ID NO 8
<211> LENGTH: 97
<212> TYPE: DNA
<213> ORGANISM: artificial sequences
<220> FEATURE:
<221> NAME/KEY: source
<222> LOCATION: 1..97
<223> OTHER INFORMATION: /mol_type="DNA"
      /note="DNA for shRNA probe"
      /organism="artificial sequences"

<400> SEQUENCE: 8
tgctgttgac agtgagcgcg caatatgcct ccttgtatta tagtgaagcc acagatgtat    60
aatacaagga ggcatattgc ttgcctactg cctcgga                             97

<210> SEQ ID NO 9
<211> LENGTH: 97
<212> TYPE: DNA
<213> ORGANISM: artificial sequences
<220> FEATURE:
<221> NAME/KEY: source
<222> LOCATION: 1..97
<223> OTHER INFORMATION: /mol_type="DNA"
      /note="DNA for shRNA"
      /organism="artificial sequences"

<400> SEQUENCE: 9
tgctgttgac agtgagcgcg gacaactaaa gatttctcaa tagtgaagcc acagatgtat    60
tgagaaatct ttagttgtcc atgcctactg cctcgga                             97

<210> SEQ ID NO 10
<211> LENGTH: 97
<212> TYPE: DNA
<213> ORGANISM: artificial sequences
<220> FEATURE:
<221> NAME/KEY: source
<222> LOCATION: 1..97
<223> OTHER INFORMATION: /mol_type="DNA"
      /note="DNA for shRNA"
      /organism="artificial sequences"

<400> SEQUENCE: 10
tgctgttgac agtgagcgcg ggcatttaat tcatctttaa tagtgaagcc acagatgtat    60
taaagatgaa ttaaatgccc atgcctactg cctcgga                             97

-continued

```
<210> SEQ ID NO 11
<211> LENGTH: 97
<212> TYPE: DNA
<213> ORGANISM: artificial sequences
<220> FEATURE:
<221> NAME/KEY: source
<222> LOCATION: 1..97
<223> OTHER INFORMATION: /mol_type="DNA"
      /note="DNA for shRNA"
      /organism="artificial sequences"

<400> SEQUENCE: 11
tgctgttgac agtgagcgcc caatgcattt cctggagaat tagtgaagcc acagatgtaa      60
ttctccagga aatgcattgg ttgcctactg cctcgga                              97

<210> SEQ ID NO 12
<211> LENGTH: 97
<212> TYPE: DNA
<213> ORGANISM: artificial sequences
<220> FEATURE:
<221> NAME/KEY: source
<222> LOCATION: 1..97
<223> OTHER INFORMATION: /mol_type="DNA"
      /note="DNA for shRNA"
      /organism="artificial sequences"

<400> SEQUENCE: 12
tgctgttgac agtgagcgac catattgctc ttcatatcat tagtgaagcc acagatgtaa      60
tgatatgaag agcaatatgg ctgcctactg cctcgga                              97

<210> SEQ ID NO 13
<211> LENGTH: 97
<212> TYPE: DNA
<213> ORGANISM: artificial sequences
<220> FEATURE:
<221> NAME/KEY: source
<222> LOCATION: 1..97
<223> OTHER INFORMATION: /mol_type="DNA"
      /note="DNA for shRNA"
      /organism="artificial sequences"

<400> SEQUENCE: 13
tgctgttgac agtgagcgac gtgccctact tgagaacatt tagtgaagcc acagatgtaa      60
atgttctcaa gtagggcacg ctgcctactg cctcgga                              97

<210> SEQ ID NO 14
<211> LENGTH: 97
<212> TYPE: DNA
<213> ORGANISM: artificial sequences
<220> FEATURE:
<221> NAME/KEY: source
<222> LOCATION: 1..97
<223> OTHER INFORMATION: /mol_type="DNA"
      /note="DNA for shRNA"
      /organism="artificial sequences"

<400> SEQUENCE: 14
tgctgttgac agtgagcgac catcatccta gtgggaacta tagtgaagcc acagatgtat      60 agttccccact aggatgatgg gtgcctactg cctcgga                             97

<210> SEQ ID NO 15
<211> LENGTH: 97
<212> TYPE: DNA
<213> ORGANISM: artificial sequences
<220> FEATURE:
<221> NAME/KEY: source
```

```
<222> LOCATION: 1..97
<223> OTHER INFORMATION: /mol_type="DNA"
      /note="DNA for shRNA"
      /organism="artificial sequences"

<400> SEQUENCE: 15
tgctgttgac agtgagcgcc cgagcactga actttgcaaa tagtgaagcc acagatgtat    60
ttgcaaagtt cagtgctcgg ttgcctactg cctcgga                            97

<210> SEQ ID NO 16
<211> LENGTH: 21
<212> TYPE: DNA
<213> ORGANISM: artificial sequences
<220> FEATURE:
<221> NAME/KEY: source
<222> LOCATION: 1..21
<223> OTHER INFORMATION: /mol_type="DNA"
      /note="DNA for siRNA probe, sense strand"
      /organism="artificial sequences"

<400> SEQUENCE: 16
taacggccta gacattcaat t                                             21

<210> SEQ ID NO 17
<211> LENGTH: 21
<212> TYPE: DNA
<213> ORGANISM: artificial sequences
<220> FEATURE:
<221> NAME/KEY: source
<222> LOCATION: 1..21
<223> OTHER INFORMATION: /mol_type="DNA"
      /note="DNA for siRNA probe, antisense strand"
      /organism="artificial sequences"

<400> SEQUENCE: 17
ttgaatgtct aggccgttat t                                             21

<210> SEQ ID NO 18
<211> LENGTH: 21
<212> TYPE: DNA
<213> ORGANISM: artificial sequences
<220> FEATURE:
<221> NAME/KEY: source
<222> LOCATION: 1..21
<223> OTHER INFORMATION: /mol_type="DNA"
      /note="DNA for siRNA probe, sense strand"
      /organism="artificial sequences"

<400> SEQUENCE: 18
ggatgatgat gatgatgatt t                                             21

<210> SEQ ID NO 19
<211> LENGTH: 21
<212> TYPE: DNA
<213> ORGANISM: artificial sequences
<220> FEATURE:
<221> NAME/KEY: source
<222> LOCATION: 1..21
<223> OTHER INFORMATION: /mol_type="DNA"
      /note="DNA for siRNA probe, antisense strand"
      /organism="artificial sequences"

<400> SEQUENCE: 19
atcatcatca tcatcatcct t                                             21

<210> SEQ ID NO 20
<211> LENGTH: 97
<212> TYPE: DNA
```

```
<213> ORGANISM: artificial sequences
<220> FEATURE:
<221> NAME/KEY: source
<222> LOCATION: 1..97
<223> OTHER INFORMATION: /mol_type="DNA"
      /note="DNA for shRNA probe"
      /organism="artificial sequences"

<400> SEQUENCE: 20
tgctgttgac agtgagcgag gcctagacat tcaagacaaa tagtgaagcc acagatgtat    60
ttgtcttgaa tgtctaggcc gtgcctactg cctcgga                             97

<210> SEQ ID NO 21
<211> LENGTH: 97
<212> TYPE: DNA
<213> ORGANISM: artificial sequences
<220> FEATURE:
<221> NAME/KEY: source
<222> LOCATION: 1..97
<223> OTHER INFORMATION: /mol_type="DNA"
      /note="DNA for shRNA probe"
      /organism="artificial sequences"

<400> SEQUENCE: 21
tgctgttgac agtgagcgac ccaagaaaga gctgattatt tagtgaagcc acagatgtaa    60
ataatcagct ctttcttggg ctgcctactg cctcgga                             97

<210> SEQ ID NO 22
<211> LENGTH: 57
<212> TYPE: DNA
<213> ORGANISM: artificial sequences
<220> FEATURE:
<221> NAME/KEY: source
<222> LOCATION: 1..57
<223> OTHER INFORMATION: /mol_type="DNA"
      /note="DNA for shRNA probe"
      /organism="artificial sequences"

<400> SEQUENCE: 22
ccggccaaga aagagctgat tattactcga gtaataatca gctctttctt ggttttt       57

<210> SEQ ID NO 23
<211> LENGTH: 57
<212> TYPE: DNA
<213> ORGANISM: artificial sequences
<220> FEATURE:
<221> NAME/KEY: source
<222> LOCATION: 1..57
<223> OTHER INFORMATION: /mol_type="DNA"
      /note="DNA for shRNA probe"
      /organism="artificial sequences"

<400> SEQUENCE: 23 ccggggttctg gatgtgttgg agtttctcga gaaactccaa cacatccaga actttttt    57

<210> SEQ ID NO 24
<211> LENGTH: 57
<212> TYPE: DNA
<213> ORGANISM: artificial sequences
<220> FEATURE:
<221> NAME/KEY: source
<222> LOCATION: 1..57
<223> OTHER INFORMATION: /mol_type="DNA"
      /note="DNA for shRNA probe"
      /organism="artificial sequences"

<400> SEQUENCE: 24
ccggcgatga gaaataccag cactactcga gtagtgctgg tatttctcat cgttttt       57
```

<210> SEQ ID NO 25
<211> LENGTH: 57
<212> TYPE: DNA
<213> ORGANISM: artificial sequences
<220> FEATURE:
<221> NAME/KEY: source
<222> LOCATION: 1..57
<223> OTHER INFORMATION: /mol_type="DNA"
      /note="DNA for shRNA probe"
      /organism="artificial sequences"

<400> SEQUENCE: 25
ccgggcgatc ctaagaagaa atatactcga gtatatttct tcttaggatc gctttttt    57

<210> SEQ ID NO 26
<211> LENGTH: 57
<212> TYPE: DNA
<213> ORGANISM: artificial sequences
<220> FEATURE:
<221> NAME/KEY: source
<222> LOCATION: 1..57
<223> OTHER INFORMATION: /mol_type="DNA"
      /note="DNA for shRNA probe"
      /organism="artificial sequences"

<400> SEQUENCE: 26
ccggcttctc ccatttcctg atctactcga gtagatcagg aaatgggaga agttttt    57

<210> SEQ ID NO 27
<211> LENGTH: 97
<212> TYPE: DNA
<213> ORGANISM: artificial sequences
<220> FEATURE:
<221> NAME/KEY: source
<222> LOCATION: 1..97
<223> OTHER INFORMATION: /mol_type="DNA"
      /note="DNA for shRNA probe"
      /organism="artificial sequences"

<400> SEQUENCE: 27
tgctgttgac agtgagcgcc ctggacaact tcatcaagat tagtgaagcc acagatgtaa    60
tcttgatgaa gttgtccagg ttgcctactg cctcgga                            97

<210> SEQ ID NO 28
<211> LENGTH: 97
<212> TYPE: DNA
<213> ORGANISM: artificial sequences
<220> FEATURE:
<221> NAME/KEY: source
<222> LOCATION: 1..97
<223> OTHER INFORMATION: /mol_type="DNA"
      /note="DNA for shRNA probe "
      /organism="artificial sequences"

<400> SEQUENCE: 28
tgctgttgac agtgagcgac ctcaaagcca tgaagatgat tagtgaagcc acagatgtaa    60
tcatcttcat ggctttgagg gtgcctactg cctcgga                            97

<210> SEQ ID NO 29
<211> LENGTH: 51
<212> TYPE: DNA
<213> ORGANISM: artificial sequences
<220> FEATURE:
<221> NAME/KEY: source
<222> LOCATION: 1..51
<223> OTHER INFORMATION: /mol_type="DNA"
      /note="DNA for shRNA probe"

```
                /organism="artificial sequences"

<400> SEQUENCE: 29
acttcatcaa gattggcgag ttcaagagac tcgccaatct tgatgaagtt t           51

<210> SEQ ID NO 30
<211> LENGTH: 97
<212> TYPE: DNA
<213> ORGANISM: artificial sequences
<220> FEATURE:
<221> NAME/KEY: source
<222> LOCATION: 1..97
<223> OTHER INFORMATION: /mol_type="DNA"
      /note="DNA for shRNA probe"
      /organism="artificial sequences"

<400> SEQUENCE: 30
tgctgttgac agtgagcgcg caatgaagag taaccgttaa tagtgaagcc acagatgtat          60
taacggttac tcttcattgc ttgcctactg cctcgga                                  97
```